(12) United States Patent
Hopenfeld

(10) Patent No.: US 9,943,244 B2
(45) Date of Patent: Apr. 17, 2018

(54) WAVEFORM FEATURE VALUE AVERAGING SYSTEM AND METHODS FOR THE DETECTION OF CARDIAC EVENTS

(75) Inventor: Bruce Hopenfeld, Salt Lake City, UT (US)

(73) Assignee: Angel Medical Systems, Inc., Tinton Falls, NJ (US)

( * ) Notice: Subject to any disclaimer, the term of this patent is extended or adjusted under 35 U.S.C. 154(b) by 1608 days.

(21) Appl. No.: 11/898,673

(22) Filed: Sep. 14, 2007

(65) Prior Publication Data

US 2009/0076403 A1 Mar. 19, 2009

(51) Int. Cl.
*A61B 5/0472* (2006.01)
*A61B 5/00* (2006.01)

(52) U.S. Cl.
CPC .......... *A61B 5/0472* (2013.01); *A61B 5/7239* (2013.01)

(58) Field of Classification Search
USPC ................ 600/508, 509, 516, 517, 515, 518
See application file for complete search history.

(56) References Cited

U.S. PATENT DOCUMENTS

| | | | |
|---|---|---|---|
| 4,989,610 A * | 2/1991 | Patton et al. | 600/508 |
| 5,046,504 A | 9/1991 | Albert et al. | |
| 5,817,027 A * | 10/1998 | Arand et al. | 600/515 |
| 6,397,100 B2 | 5/2002 | Stadler et al. | |
| 6,480,733 B1 * | 11/2002 | Turcott | 600/516 |
| 6,663,572 B2 * | 12/2003 | Starobin et al. | 600/508 |
| 6,721,592 B2 * | 4/2004 | Peichel et al. | 600/509 |
| 2002/0042578 A1 * | 4/2002 | Starobin et al. | 600/508 |

(Continued)

OTHER PUBLICATIONS

Bosnjak, A., et al.; "An Approach to Intelligent Ischaemia Monitoring"; Medical & Biological Enginnering & Computing; Nov. 1995; pp. 749-756.

(Continued)

*Primary Examiner* — Allen Porter, Jr.
(74) *Attorney, Agent, or Firm* — Rosenberg, Klein & Lee

(57) ABSTRACT

Disclosed is a system for detecting pathophysiological cardiac conditions. The system comprises a diagnostic device that contains electronic circuitry that can detect a cardiac event such as an acute ischemia. The cardiac diagnostic device receives electrical signals from subcutaneous or body surface sensors. The cardiac diagnostic device includes a processor that computes QRS onset and offset points and fiducial points associated with T and U waves. The processor than baseline corrects the original signal/waveform by fitting a polynomial function to QRS offset points, and subtracting this function from the original waveform. Based on the baseline adjusted signal and/or the above mentioned fiducial points, the processor then computes averages of various waveform feature values, including a QRS measure sensitive to QRS curvature, T wave timing measures, ST segment deviation (difference between signal amplitudes at QRS offset and onset and/or minimum amplitude between QRS offset and peak T wave); and T/U wave amplitudes. These averages are computed by exponential averaging. From the exponential averages, the processor computes an average of the change in the averages over time. Based on the averages and the change in the averages, the processor applies an ischemia test to determine a likelihood of ischemia.

7 Claims, 17 Drawing Sheets

(56) References Cited

U.S. PATENT DOCUMENTS

| | | | |
|---|---|---|---|
| 2002/0165459 A1* | 11/2002 | Starobin et al. | 600/509 |
| 2003/0083583 A1* | 5/2003 | Kovtun et al. | 600/509 |
| 2004/0116972 A1* | 6/2004 | Marcovecchio | 607/14 |
| 2005/0027202 A1* | 2/2005 | Ginzburg et al. | 600/509 |
| 2005/0038351 A1* | 2/2005 | Starobin et al. | 600/516 |
| 2005/0165319 A1* | 7/2005 | Brodnick et al. | 600/509 |
| 2005/0222507 A1* | 10/2005 | Logan et al. | 600/509 |
| 2007/0142732 A1 | 6/2007 | Brockway et al. | |
| 2007/0179383 A1 | 8/2007 | Cho et al. | |

OTHER PUBLICATIONS

Arini, et al.; "Evolution of T Wave Width During Severe Ischemia Generated by Percutaneous Transluminal Coronary Angioplasty"; Computers in Cardiology 2006; 33:713-716.

Badilini, et al.: "QT interval analysis on ambulatory electrocardiogram recordings: a selective beat averaging approach"; Medical Biological Engineering & Computing; Jan. 1999, 37(1):71-9.

Cantor, et al.; "QRS prolongation measured by a new computerized method: a sensitive marker for detecting exercise-induced ischemia"; Cardiology; Sep.-Oct. 1997, 88(5):446-52.

Hayn, et al.; "Automated QT Interval Measurement from Multilead ECG Signals"; Comp. Card.; 33:38 1-4, 2006.

Kemmelings, et. al.; "Automatic QRS onset and offset detection for body surface QRS integral mapping of ventricular tachycardia"; IEEE Transactions on Biomedical Engineering; 1994, 41:830-836.

Lander, et al.; "Abnormal intra-QRS potentials associated with percutaneous transluminal coronary angiography-induced transient myocardial ischemia"; Journal of Electrocardiology; Jul. 2006, 39(3):282-289.

Miller, et al; "Total body surface potential mapping during exercise: QRS-T-wave changes in normal young adults"; Circulation; 62(3):632-645, 1980.

Papaloukas, et al.; "Automated methods for ischemia detection in long-duration ECGs"; Cardiovasc Rev Rep; 24(6):313-320, 2003.

Pettersson, et al.; "Changes in high-frequency QRS components are more sensitive than ST-segment deviation for detecting acute coronary artery occlusion"; Journal of the American College of Cardiology; Nov. 15, 2000, 36(6): 1827-1834.

Pueyo, et al.; "High-Frequency Signature of the QRS Complex across Ischemia Quantified by QRS Slopes"; Computers in Cardiology 2005; 32:659-662.

Sun, et al.; "Characteristic wave detection in ECG signal using morphological transform"; BMC Cardiovascular Disorder; 2005; 5:28, http://www.biomedcentral.com/1471-2261/5/28.

Zong, et al.; "A robust open-source algorithm to detect onset and duration of QRS complexes"; Computers in Cardiology 2003; 30:737-740.

* cited by examiner

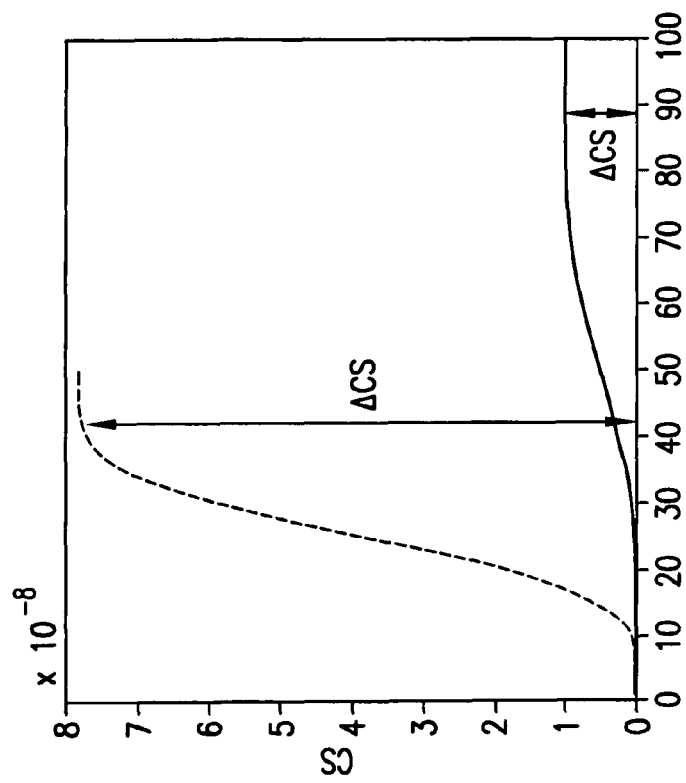
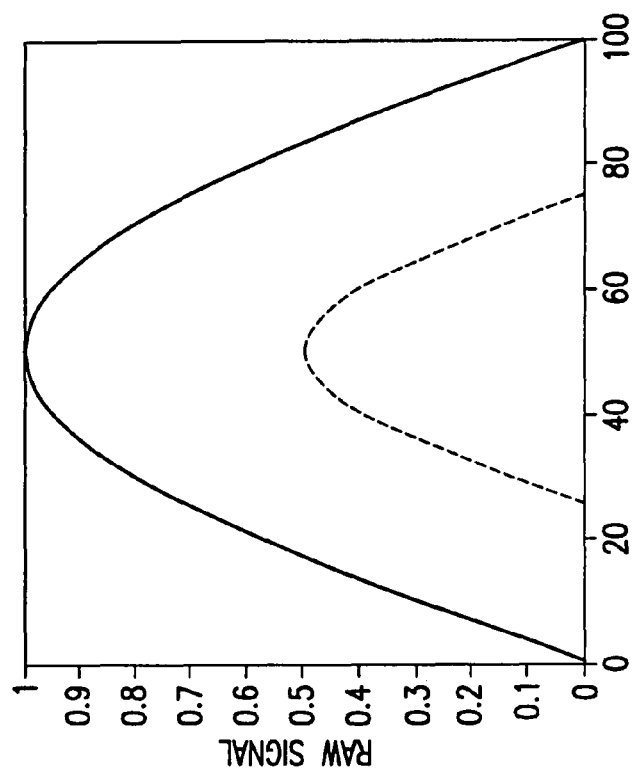
FIG. 13b
FIG. 13a

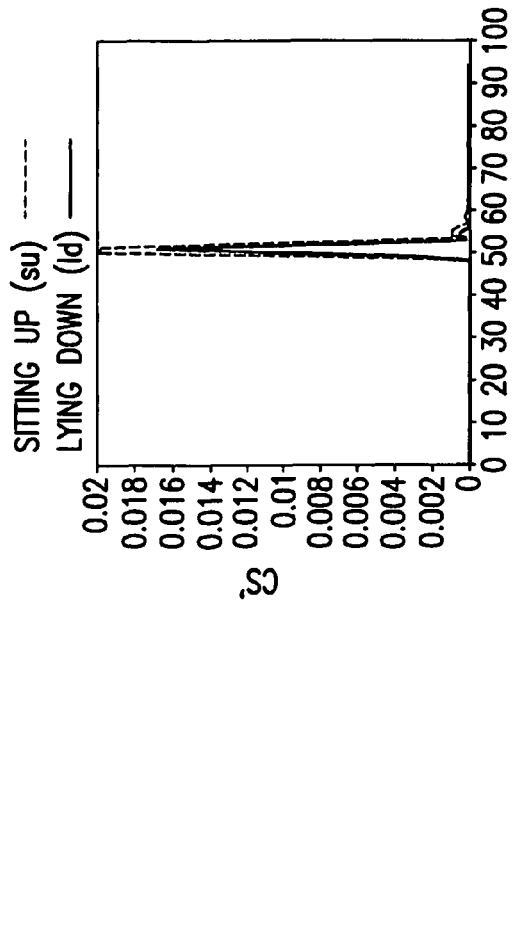
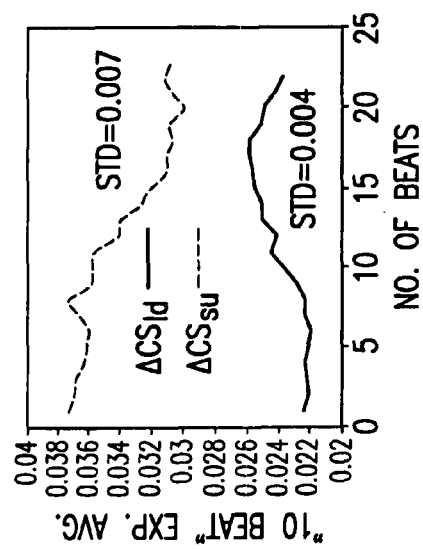
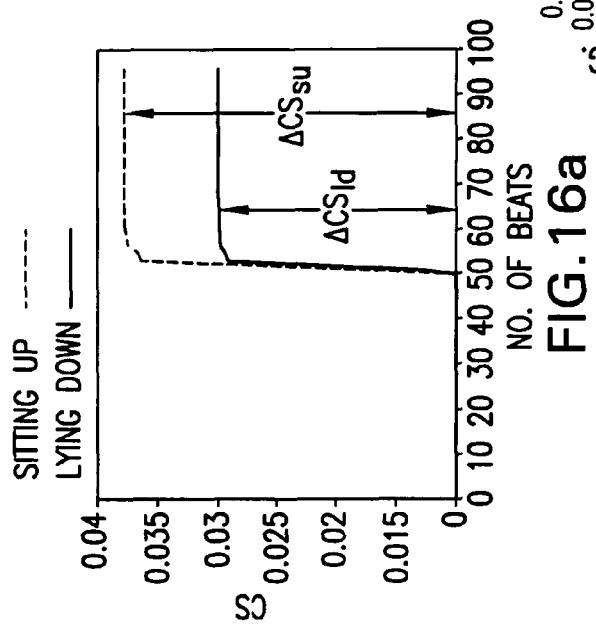
FIG. 16b
FIG. 16c
FIG. 16a

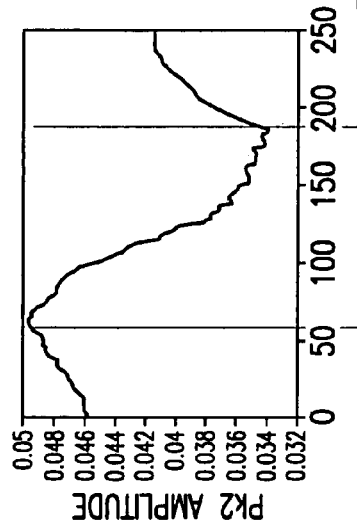
FIG.18a
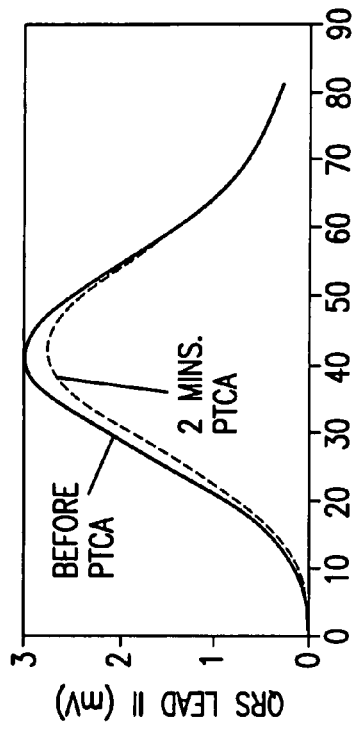
FIG.18c
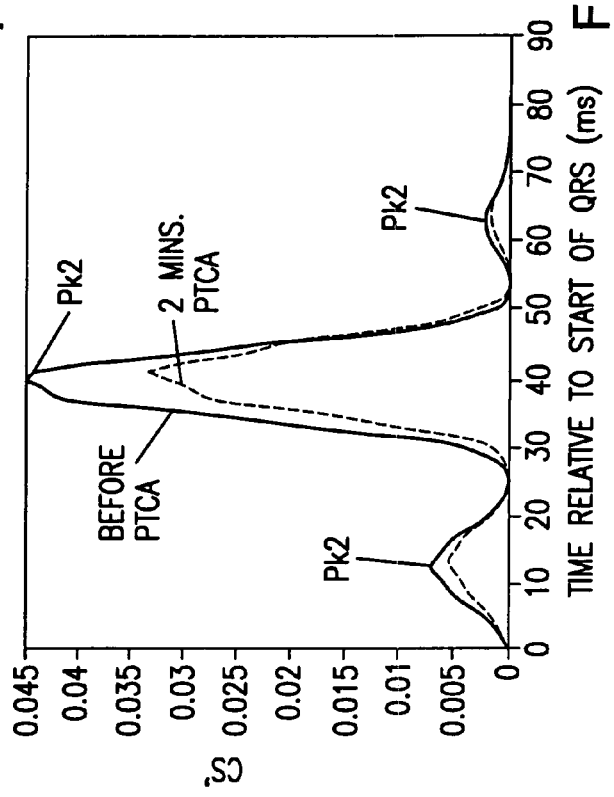
FIG.18b
FIG.18d

WAVEFORM FEATURE VALUE AVERAGING SYSTEM AND METHODS FOR THE DETECTION OF CARDIAC EVENTS

FIELD OF USE

This invention is in the field of medical device systems that monitor a patient's cardiovascular condition.

BACKGROUND OF THE INVENTION

Heart disease is the leading cause of death in the United States. A heart attack, also known as an acute myocardial infarction (AMI), typically results from a blood clot or "thrombus" that obstructs blood flow in one or more coronary arteries. AMI is a common and life-threatening complication of coronary artery disease. Coronary ischemia is caused by an insufficiency of oxygen to the heart muscle. Ischemia is typically provoked by physical activity or other causes of increased heart rate when one or more of the coronary arteries is narrowed by atherosclerosis. AMI, which is typically the result of a completely blocked coronary artery, is the most extreme form of ischemia. Patients will often (but not always) become aware of chest discomfort, known as "angina", when the heart muscle is experiencing ischemia. Those with coronary atherosclerosis are at higher risk for AMI if the plaque becomes further obstructed by thrombus.

There are a number of portable monitors that attempt to detect AMI. Monitors that include wearable sensors (e.g. a medical-vest with electrodes) may be somewhat inconvenient for patients. Chronically implanted sensors provide the possibility for continuous monitoring without many of the inconveniences associated with wearable monitors. One type of implantable monitor includes an electrode chronically implanted within the heart. An intracardiac electrode may provide a strong signal at the cost of requiring intracardiac implantation. Another type of implantable monitor can rely upon subcutaneous electrodes, which are less invasive, but receive smaller amplitude signals compared to intracardiac electrodes.

Furthermore, subcutaneous electrodes require lead structures to connect them to the monitoring device. If the lead is also subcutaneous, it is generally desirable to keep it as short as possible. Shorter leads provide a more limited view of the torso's electrical field, which may in turn compromise the ability of a monitoring device to detect certain types of cardiac events. It would be desirable to have a subcutaneous electrode and lead system with relatively short leads that can diagnose a variety of cardiac conditions, including ischemia associated with significant occlusions of any of the three major coronary arteries, the left anterior descending artery, the left circumflex artery and the right coronary artery.

U.S. patent application Ser. No. 11/889,752, entitled "SYSTEM AND METHODS FOR DETECTING ISCHEMIA WITH A LIMITED EXTRACARDIAC LEAD SET", filed 16 Aug. 2007, ("Limited Lead Set Application") assigned to the assignee of the present application, discloses (inter alia) a two lead system with one lead extending from the anterior precordial region to the lower left side and the other extending from the anterior/superior region to the right of the first lead to the inferior right side. The '752 application describes a number of prior devices/techniques for detecting ischemia based on extracardiac electrical recordings.

Heart rate corrected QT and JT intervals, known as QTc and JTc respectively, have been widely used to assess cardiac repolarization, which is affected by many different types of pathologies, including acute ischemia. The QT and JT intervals are the times between the end of the T wave and the onset of the Q wave and J point, respectively. QT interval analysis on ambulatory electrocardiogram recordings: a selective beat averaging approach. With regard to ambulatory recordings, a number of beats may be averaged together to derive a representative beat whose QT interval is measured. (E.g. see Badilini et al., "QT interval analysis on ambulatory electrocardiogram recordings: a selective beat averaging approach," Med Biol Eng Comput. 1999 January; 37(1):71-9.) Signal averaging requires the alignment of different beats and generally also requires the removal of beats that don't fit a template; these steps are somewhat computationally expensive.

Sun et al. ("Characteristic wave detection in ECG signal using morphological transform"; BMC Cardiovasc Disord. 2005; 5: 28) describe a multi-scale derivative method for locating QRS (and P and T) wave fiducial points. "Long distance" derivatives/differences (e.g. f(x+n)−f(x), where n>1) are taken both before and after each candidate onset point and the difference between these derivatives is calculated to form a type of second derivative/difference which the authors term a "multiscale morphological derivative transform." QRS onset or other fiducial points are defined as the maxima or minima of this "transform." Kemmelings et. al. describe a QRS onset/offset detection scheme that involves summing the absolute value of the first derivative (difference) and then taking a "long distance" derivative of this summed signal, to find where it abruptly changes (over a large scale). ("Automatic QRS onset and offset detection for body surface Q RS integral mapping of ventricular tachycardia."; IEEE Trans Biomed Eng. 1994; 41:830-836). Hayn et al., Automated QT Interval Measurement from Multilead ECG Signals. Comp. Card. 33:3814, 2006 describe a method for detecting Q wave onset by iteratively selecting possible QRS onset points by finding, for each step in the iteration, the point characterized by the "most distinct change in the range curve" around the point. T wave offsets were also found by this method, as well as by fitting a Guassian curve to the T wave and defining the offset with respect to the standard deviation of the curve.

Zong et al. (A robust open-source algorithm to detect onset and duration of QRS complexes, Computers in Cardiology, 2003, Issue, 21-24 Sep. 2003, Page(s): 737-740) describe a method for detecting QRS onset and offset points by using a function that corresponds to the "distance" by the signal; the function has the form $(D^2+(\Delta s/\Delta t)^2)^{0.5}$, where D is a constant and $\Delta s$ is the difference between successive samples of an ECG signal and $\Delta t$ is the time between samples (i.e. the inverse of the sampling frequency). This function is essentially a discrete version of the calculus formula for distance along a curve, which is based on the first derivative of the curve.

Arini et al. (Evolution of T Wave Width During Severe Ischemia Generated by Percutaneous Transluminal Coronary Angioplasty, Computers in Cardiology 2006; 33:713-716), describe methods for assessing the presence/severity of ischemia based on T wave width, which in turn requires a computation of T wave onset and offset times.

In U.S. Pat. No. 6,397,100 to Stadler and Shannon, ST segment values are low pass filtered to ensure that very rapid changes, which may be caused by axis shifts, are not considered to be ST shifts caused by ischemia. Two different low pass filters are applied, resulting in two different filtered signals. One filtered signal is representative of very slow ST baseline drift. The other filtered signal is representative of the true ST level excluding high frequency axis shift. ST segment deviation indicative of ischemia is equal to the difference between the filtered signals.

In healthy persons, increases in heart rate generally decrease QRS amplitudes (see Miller et al, Circulation; 62(3):632-645, 1980) and decrease QRS duration (Cantor A et al., "QRS prolongation measured by a new computerized method: a sensitive marker for detecting exercise-induced ischemia", Cardiology. 1997 September-October; 88(5): 446-52). (These changes are consistent with an exercise induced reduction in action potential amplitude and increase in cell resting potential.) As a result of these changes, the high frequency content of the QRS in normals tends to increase with increasing heart rate. Some data indicates the high frequency QRS content of ischemic patients decreases with increases in heart rate and also decreases during balloon angioplasty/acute ischemia. (Pettersson et al., "Changes in high-frequency QRS components are more sensitive than ST-segment deviation for detecting acute coronary artery occlusion." J Am Coll Cardiol. 2000 Nov. 15; 36(6): 1827-34.)

Consequently, the high frequency content of the QRS has been proposed as a marker of ischemia. To derive a measure of the high frequency QRS spectral content, Pettersson et al. disclose the steps of isolating QRS complexes, signal averaging them, and then passing them through a filter with a passband of 150-250 Hz. The root mean square value of the resulting filtered QRS is then obtained. Another method of analyzing high frequency QRS content involves a search for portions within the envelope of the filtered QRS signal that have a smaller amplitude in comparison with neighboring portions of the filtered QRS, i.e. these "reduced amplitude zones" constitute a trough in between peaks of the filtered QRS.

Pueyo et al. ("High-Frequency Signature of the QRS Complex across Ischemia Quantified by QRS Slopes", Computers in Cardiology 2005; 32:659-662) describe a method for examining the R and S wave slopes and amplitudes, associated with the standard 12 lead electrocardiogram leads, during balloon occlusions. The maximum local upslope and downslope points are determined and lines are fitted in a least squares sense to the 15 ms windows surrounding these points. The slopes of these lines are the ischemia markers.

Lander et al. ("Abnormal intra-QRS potentials associated with percutaneous transluminal coronary angiography-induced transient myocardial ischemia"; J. Electrocardiol. 2006 July; 39(3):282-9) describe a method for determining the presence of slurs or notches in the QRS complex; the presence of such abnormal intra-QRS potentials is indicative of ischemia (or other abnormalities affecting conduction). The QRS is transformed into the frequency domain and then effectively separated into a deterministic/smooth portion and a residual/unpredictable portion. The deterministic/smooth portion is transformed back into the time domain and subtracted from the original QRS, leaving a time domain residual QRS representative of abnormal notches, slurs or the like.

In U.S. Pat. No. 5,046,504, Albert et al. disclose a method for performing a frequency analysis (e.g. by FFT) of overlapping portions of the QRS complex, thereby deriving a "spectro-temporal map" that shows how the frequency content of the QRS changes over the course of the QRS. The '504 patent describes various methods for displaying spectro-temporal maps and information extracted therefrom. The '504 patent also describes methods for determining the presence of "late-potentials" from the spectro-temporal maps and information extracted therefrom.

Despite all of the foregoing work that has been done, there is still a need for an effective subcutaneous or surface based system for monitoring ischemia.

SUMMARY OF THE INVENTION

An embodiment of the present invention comprises a system that includes of an implanted cardiac detection and/or diagnostic device and external equipment. The battery powered implantable cardiac diagnostic device contains electronic circuitry that can detect a cardiac event such as an acute myocardial infarction and warn the patient when the event, or a clinically relevant precursor, occurs. The cardiac diagnostic device can store the patient's electrogram for later readout and can send wireless signals to and receive wireless signals from the external equipment.

The cardiac diagnostic device receives electrical signals from subcutaneous or body surface sensors. One pair of electrodes comprises a lead sensor that senses the potential between the upper right clavicle and a medial region over the area of the sternum. Such a lead is oriented substantially along the long axis of the heart and is therefore capable of detecting current flow between the epicardium and endocardium, which at least in part dictates T wave timing.

The cardiac diagnostic device includes a processor that computes QRS onset and offset points and fiducial points associated with T and U waves. The processor than baseline corrects the original signal/waveform by fitting a polynomial function to QRS offset points, and subtracting this function from the original waveform.

Based on the baseline adjusted signal and/or the above mentioned fiducial points, the processor then computes averages of various waveform feature values, including a QRS measure sensitive to QRS curvature, T wave timing measures, ST segment deviation (difference between signal amplitudes at QRS offset and onset and/or minimum amplitude between QRS offset and peak T wave); and T/U wave amplitudes. These averages are preferably computed by exponential averaging. From the exponential averages, the processor computes an average of the change in the averages over time. Based on the averages and the change in the averages, the processor applies an ischemia test to determine a likelihood of ischemia.

QRS onset and offset detection is performed by selecting candidate QRS onset and offset points and selecting an optimal candidate based on a penalty function that involves various metrics pertaining to the first and second derivative of the waveform, with a bias toward making the QRS narrow. The candidate points are selected by computing a function sensitive to QRS curvature, and looking for groups of points near where the function transitions between flat and steep portions; a flat to steep transition indicates QRS onset while a steep to flat transition indicates QRS offset.

The function sensitive to wavefront curvature is the cumulative sum of a high pass filtered version of the absolute value of a second derivative (i.e. the difference of the slope function) of the original waveform. The filtering is performed by raising the absolute value of the second derivative data to the third power. The function sensitive to wavefront curvature is also used as part of an ischemia test.

BRIEF DESCRIPTION OF THE DRAWINGS

FIG. 4*c* also shows an alternative positions for electrodes in the form of a ring in the area of the upper right shoulder.

FIG. 13*a* shows two half cosine waves characterized by different frequencies. FIG. 13*b* illustrates how the present invention's waveform curvature metric, CS, reflects curvature of the waveforms shown in FIG. 13*a*.

FIG. 16*a* shows the CS of a healthy person lying down and sitting up. FIG. 16*b* shows the centered difference of the CS shown in FIG. 16*a*. FIG. 16*c* shows an exponential average of the QRS CS jump of a healthy person lying down and sitting up.

FIG. 18*a* shows another set of QRS waveforms before and 2 minutes into a balloon inflation. FIG. 18*b* shows the associated centered difference of CS (CS') profiles of these waveforms, which is characterized by 3 peaks. FIG. 18*c* shows the value of the amplitude of the second peak before, during and after a balloon inflation. FIG. 18*d* shows the value of the timing of the third peak before, during and after a balloon inflation.

DETAILED DESCRIPTION OF THE INVENTION

Figure 1:
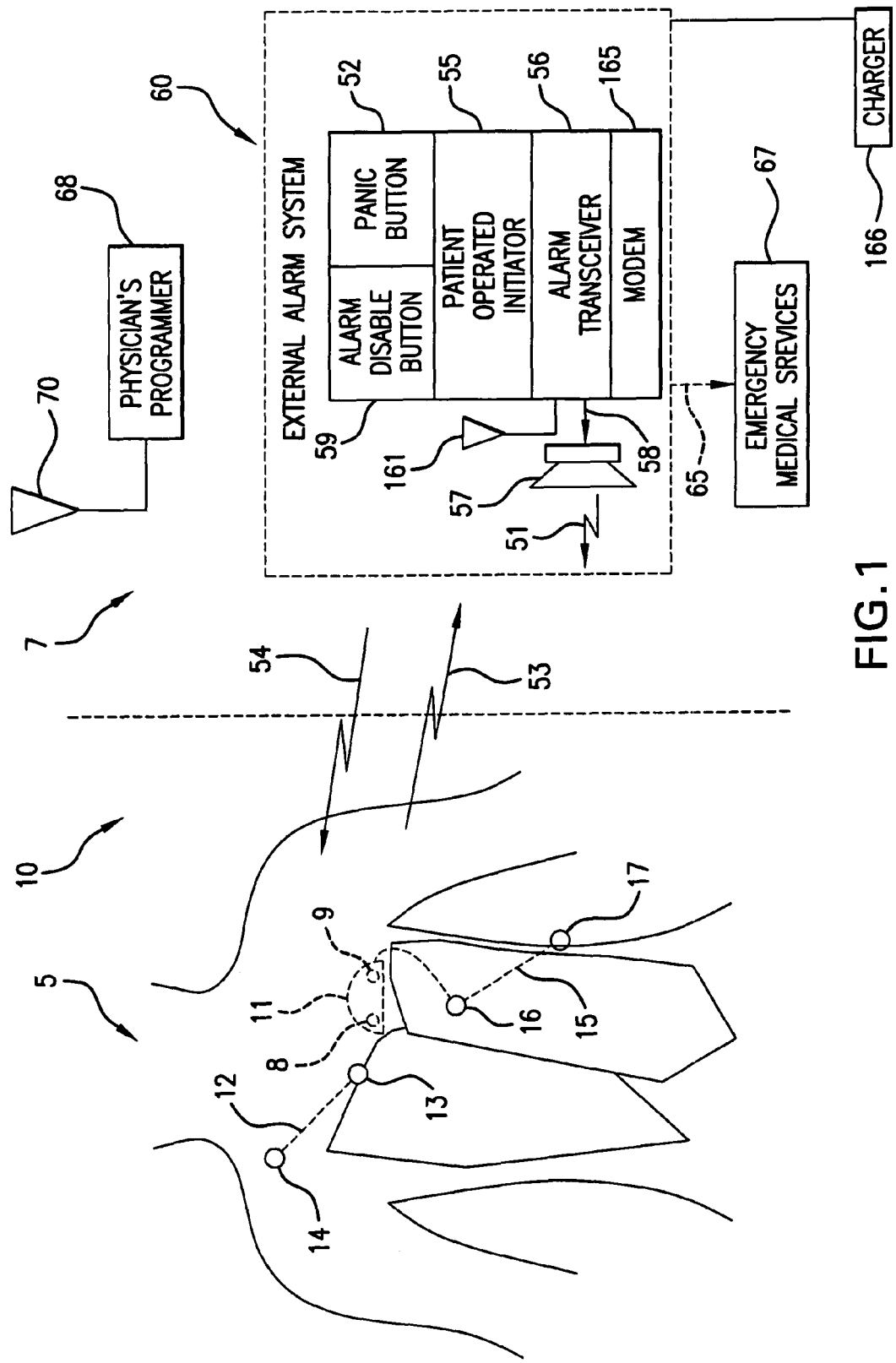
FIG. 1 illustrates a system for the detection of a cardiac event and for warning the patient that a medically relevant cardiac event is occurring.

"Lead" means at least two sensors that are configured to detect the electrical potential between two points.

An "average" or "average measure" or like phrases refers to a central tendency of a data set. Many types of measures may be used as averages, including without limitation the arithmetic mean, median, or an exponential average.

A "curvature function" maps a set of points of a time series waveform ("domain") to a set of output (curvature) values that is both correlated with the curvature of the waveform in the domain and has fewer members than the number of points in the domain. An example of a curvature function C with a set of output values with one member is $C=W(x+n)-2*W(x)+W(x-n)$, where $W(x)$ is the value of a time series waveform at sample/point x, where n is an integer, and where the set $\{x-n, x, x+n\}$ is the domain of the curvature function. In this example, there is a one to one time series correspondence between C and W. An example of a (global) curvature function without such a one to one time series correspondence is a discrete Fourier Transform of 20 samples corresponding to a 20 ms portion of a time series waveform, followed by a summation of the power spectral density over the frequency range of 150 Hz-250 Hz; this summation is correlated with the curvature of the 20 ms portion of the time series waveform. The (normal, non-truncated) discrete Fourier Transform alone is not a curvature function because its set of output values does not have fewer members than the number of points in the domain.

A "global curvature function" is a measure of the curvature of a multi-point portion of a waveform. A "global curvature function" maps all of the points within the portion to a set of output values, where the number of members in the set is less than the number of points within the portion. An example of a global curvature function was given in the definition of "curvature function".

A pathological heart condition "test based on" the value of a waveform feature means that the outcome of the test depends at least in part on an implicit or explicit comparison between the expected and actual values of that waveform feature (and/or changes in that waveform feature). A greater deviation between the expected value and the actual value is associated with an increase in the likelihood that the pathological condition exists according to the outcome of the test, assuming all other factors (if any) which affect the outcome of the test are held constant.

The "derivative" at a point of a waveform consisting of points sampled at a constant sampling rate is equivalent to the difference in the value of the waveform around that point. For example, a derivative at sample number x is $D=W(x+n)-W(x-n)$, where $W(x)$ is the value of a time series waveform at sample/point x, and where n is an integer that corresponds to the scale of the derivative.

A "portion" of a waveform is the set of one or more values of the waveform within a time interval. For example, if the values of the waveform are equal to [1 2 3] corresponding to the time points [4 5 6], respectively, the set $\{2\}$ is a portion of the waveform associated with the time points [4 5 6]. The set $\{1, 2, 3\}$ is also a portion of the waveform associated with those time points.

A "point" is identical to a sample, i.e. a discrete value of a waveform.

Architecture

FIG. 1 illustrates one embodiment of a system 10 comprising an implanted cardiac diagnostic device 5 and external equipment 7. The battery powered cardiac diagnostic device 5 contains electronic circuitry that can detect a cardiac event such as an acute myocardial infarction or arrhythmia and warn the patient when the event, or a clinically relevant precursor, occurs. The cardiac diagnostic device 5 can store the patient's electrogram for later readout and can send wireless signals 53 to and receive wireless signals 54 from the external equipment 7. The functioning of the cardiac diagnostic device 5 will be explained in greater detail with the assistance of FIG. 2.

The cardiac diagnostic device 5 receives electrical signals from subcutaneous or body surface leads 12 and 15. Right side lead 12 comprises electrodes 13 and 14 with polarity hereafter defined as the difference potential measured between electrode 13 and electrode 14. Left side lead 15 comprises electrodes 16 and 17 with polarity hereafter defined as the potential at electrode 16 minus the potential at electrode 17. The right side lead 12 measures the electrical signal between the upper right clavicle and a medial region over the area of the sternum and is therefore generally less than 15 cm long; the right side lead is approximately aligned with the long axis of the heart. The left side lead 15 measures the electrical signal between the left precordial chest region and an inferior left lateral or posterior torso position. Electrode placement will be further described below. The cardiac diagnostic device 5 is housed in a metal case 11 that can serve as another electrode. In particular, the lead 15 could effectively be temporally multiplexed so that it alternately measures the potential across electrodes 16 and 17 and the potential across the metal case 11 and the electrode 16 (or 17).

FIG. 1 also shows the external equipment 7 that consists of a physician's programmer 68 having an antenna 70, an external alarm system 60 including a charger 166. The external equipment 7 provides means to interact with the cardiac diagnostic device 5. These interactions include programming the cardiac diagnostic device 5, retrieving data collected by the cardiac diagnostic device 5 and handling alarms generated by the cardiac diagnostic device 5. The operation of these components is further described in U.S. patent application publication number 2004/0215092.

Figure 2:
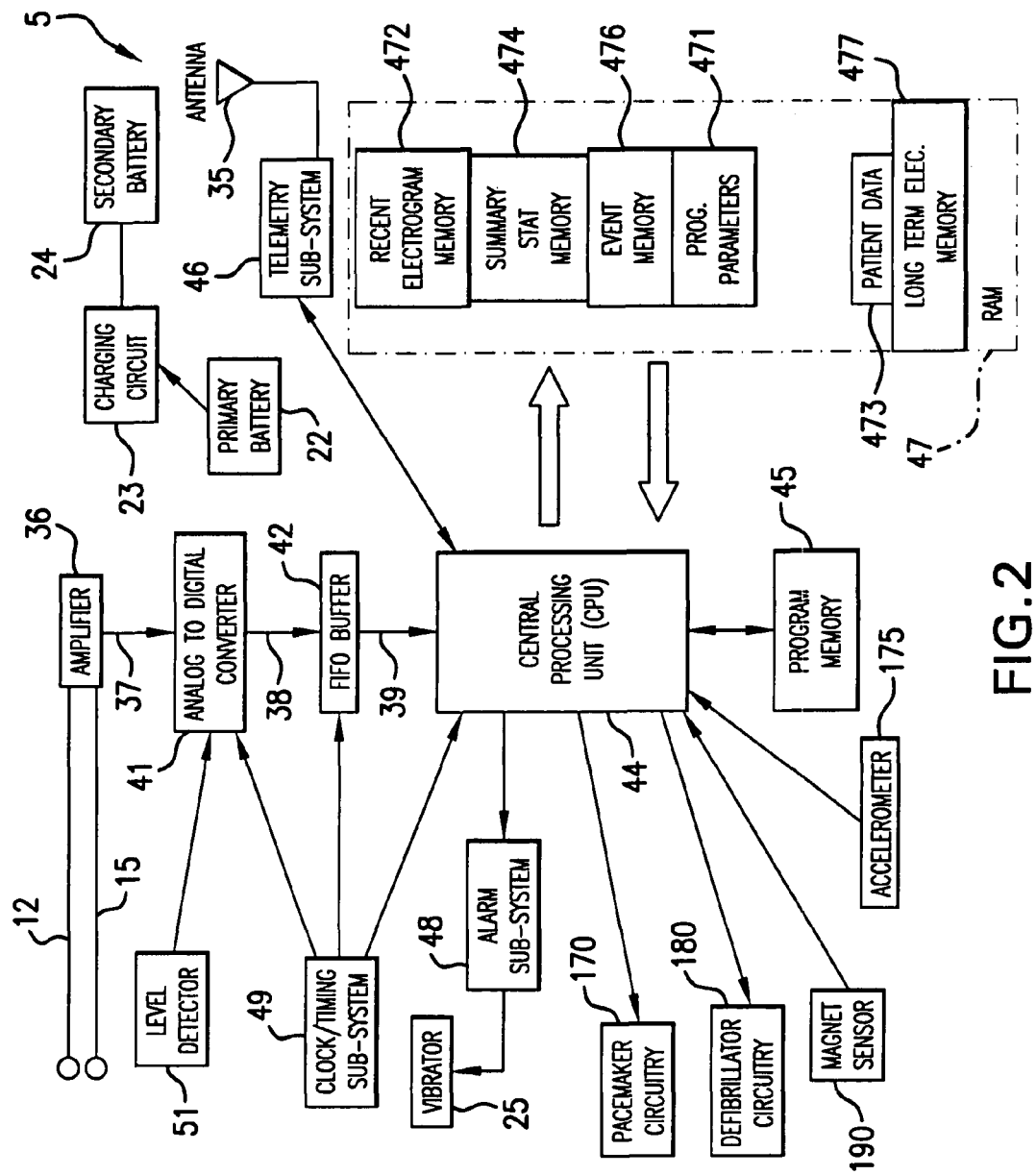
FIG. 2 is a block diagram of an implanted cardiac diagnostic system according to the present invention.

FIG. 2 is a block diagram of the cardiac diagnostic device 5 with primary battery 22 and a secondary battery 24. The secondary battery 24 is typically a rechargeable battery of smaller capacity but higher current or voltage output than the primary battery 22 and is used for short term high output components of the cardiac diagnostic device 5 like the RF chipset in the telemetry sub-system 46 or the vibrator 25 attached to the alarm sub-system 48. According to a dual battery configuration, the primary battery 22 will charge the secondary battery 24 through the charging circuit 23. The primary battery 22 is typically a larger capacity battery than the secondary battery 24. The primary battery also typically has a lower self discharge rate as a percentage of its capacity than the secondary battery 24. It is also envisioned that the secondary battery could be charged from an external induction coil by the patient or by the doctor during a periodic check-up.

The pairs of wires corresponding to leads 12 and 15 respectively connect to the amplifier 36, which is a multi-channel or differential amplifier. The amplified electrogram signals 37 from the amplifier 36 are then converted to digital signals 38 by the analog-to-digital converter 41, which preferably samples at a rate of 1000 Hz. The temporal resolution of the sampling is relevant with regard to the sampling of the high frequency components of a heartbeat's activation (QRS) complex, as will be further described below. The digital electrogram signals 38 are buffered in the First-In-First-Out (FIFO) memory 42. Processor means shown in FIG. 2 as the central processing unit (CPU) 44 coupled to memory means shown in FIG. 2 as the Random Access Memory (RAM) 47 can process the digital electrogram data 38 stored the FIFO 42 according to the programming instructions stored in the program memory 45. This programming (i.e. software) enables the cardiac diagnostic device 5 to detect the occurrence of a cardiac event such as an acute myocardial infarction.

A level detector 51 is coupled to the analog to digital converter 41. The level detector 51 detects whether a patient's torso is upright or supine and also, if the torso is supine, the extent of its rotation with respect to the earth (e.g. patient is lying flat on his/her back, lying on his/her right side or left side.) Many MEMS based level detects which can also operationally serve as inclinometers, accelerometers, and general detectors for motion/force exist.

Additional sensors may communicate with the device 5 wirelessly through the telemetry sub-system. The data from these leads may correspond to digitized electrogram signals (that have been processed by a remote subcutaneous device).

The operation of most of the components in FIG. 2 is further described in U.S. patent application publication number 2004/0215092.

In a preferred embodiment of the present invention the RAM 47 includes specific memory locations for 4 sets of electrogram segment storage. These are the recent electrogram storage 472 that would store the last 2 to 10 minutes of recently recorded electrogram segments so that the electrogram data occurring just before the onset of a cardiac event can be reviewed at a later time by the patient's physician using the physician's programmer 68 of FIG. 1. For example, the recent electrogram storage 472 might contain eight 10-second long electrogram segments that were captured every 30 seconds over the last 4 minutes.

A summary statistics memory 474 would provide storage for summary information, such as running averages, of various cardiac waveform feature values. A long term electrogram memory 477 would provide storage for electrograms collected over a relatively long period of time. In the preferred embodiment, every ninth electrogram segment that is acquired is stored in a circular buffer, so that the oldest electrogram segments are overwritten by the newest one.

The telemetry sub-system 46 with antenna 35 provides the cardiac diagnostic device 5 the means for two-way wireless communication to and from the external equipment 7 of FIG. 1. Existing radiofrequency transceiver chip sets such as the Ash transceiver hybrids produced by RF Microdevices, Inc. can readily provide such two-way wireless communication over a range of up to 10 meters from the patient. It is also envisioned that short range telemetry such as that typically used in pacemakers and defibrillators could also be applied to the cardiac diagnostic device 5. It is also envisioned that standard wireless protocols such as Bluetooth and 802.11a or 802.11b might be used to allow communication with a wider group of peripheral devices.

Electrode Positions

Orientations of the leads and the corresponding positions of electrodes 13, 14, 16 and 17 (FIG. 1) will be described with reference to FIGS. 3-4, which show body surface maps from Miller et al. (Total Body Surface Potential Mapping During Exercise: QRS-T-wave Changes in Normal Young Adults, Circulation; 62(3):632-645, 1980). A grid has been overlaid on the torso drawings to provide for a common coordinate system amongst the different torso drawings. Optimal electrode positioning is preferably patient dependent.

Figure 3A:
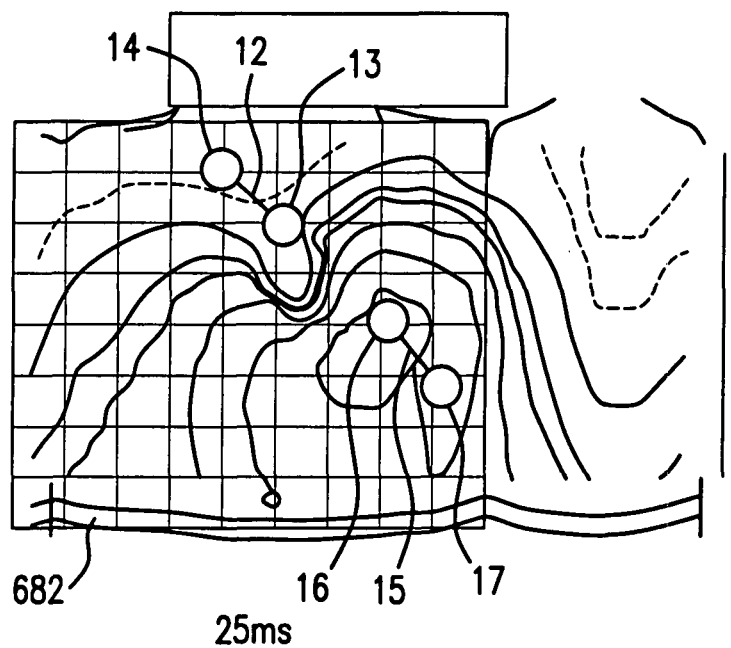
FIG. 3*a* shows a body surface map of a healthy resting individual during the early portion of the QRS complex, just after the cardiac wave has first reached the epicardial surface. Electrode positions for two leads are shown on the body surface map.

FIG. 3a shows a body surface map 682 of a healthy resting individual during the early portion of the QRS complex, just after the cardiac wave has first reached the epicardial surface ('breakthrough'). The torso is 'cut' along the right side and then unrolled, so that the left portion of the drawing represents the anterior torso and the right portion of the drawing represents the posterior torso (all of the body surface maps shown in FIGS. 3-4 show the torso in this manner). The positions of the neck and shoulders are indicated at the tops of the body surface maps.

Figure 3B:
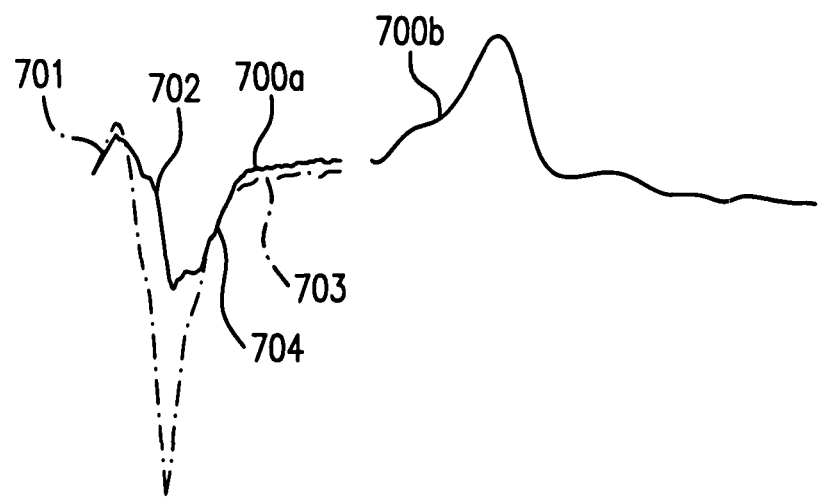
FIG. 3*b* shows a waveform that may be recorded by the upper right lead shown in FIG. 3*a*.

For a healthy individual, lead 12 (associated with electrodes 13 and 14) would be expected to record a QRS waveform similar to waveform 700a shown in FIG. 3b, which also shows the ST/T/U segments at a larger time scale 700b. For purposes of comparison, dashed waveform 703 represents a QRS recorded near the area of precordial lead v1. During early QRS, there will be a positive deflection 701 in waveform 700a. This positive deflection occurs as the cardiac wavefront envelops the endocardium and results in an endocardial/epicardial transmembrane potential gradient that produces a current flow path that is roughly aligned with the long axis of the heart ("long axis current"). Reductions in the slope/amplitude of the upstroke of waveform 701 may therefore indicate slowed conduction, which in turn may be indicative of ischemia. Conversely, the relatively delayed downstroke of waveform 701 compared to waveform 703 is a healthy indicator that long axis current continues to flow even after epicardial breakthrough of the cardiac waveform; if the downstroke 702 of waveform 701 occurred earlier, ischemia may be present in the areas (e.g. left ventricular later wall) distal to the septal sites of earliest activation. Methods for analyzing the QRS portions of the waveform 701 to assess the likelihood of ischemia will be further described below.

Figure 4A:
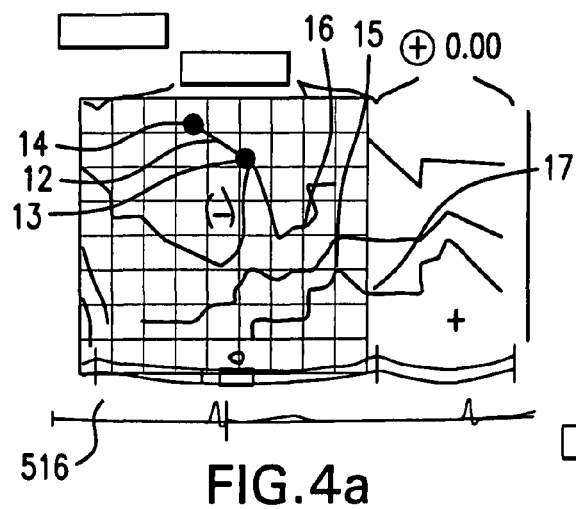
FIGS. 4*a* and 4*b* shows body surface maps and during the late QRS complex in a healthy resting person and a healthy exercising person, respectively.
Figure 4B:
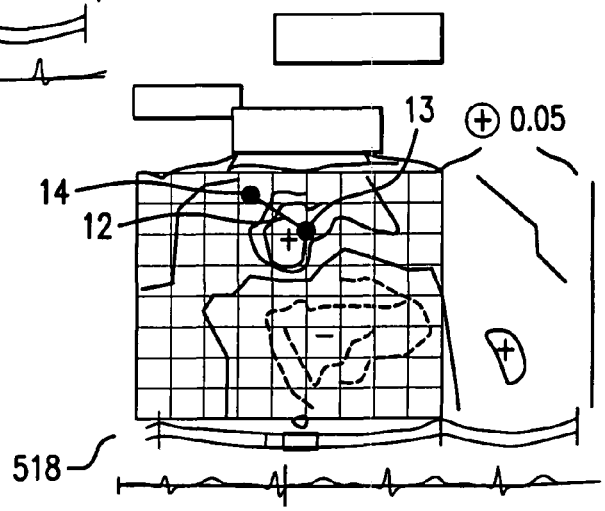

FIGS. 4a and 4b shows body surface maps 520 and 518 during the late QRS complex in a healthy resting person and a healthy exercising person, respectively. The relative time scales during which the data were recorded are indicated by a vertical line in the ECG tracings at the bottom of the maps. In a resting person, as shown in map 516, lead 12 would be expected to register a very small voltage drop during the late QRS. Conversely, in an exercising person, a more substantial positive potential (measured with electrode 13 as the positive terminal) would be expected. At higher heart rates, the absence or reduction of this positive potential may indicate a greater likelihood of ischemia.

Figure 4C:
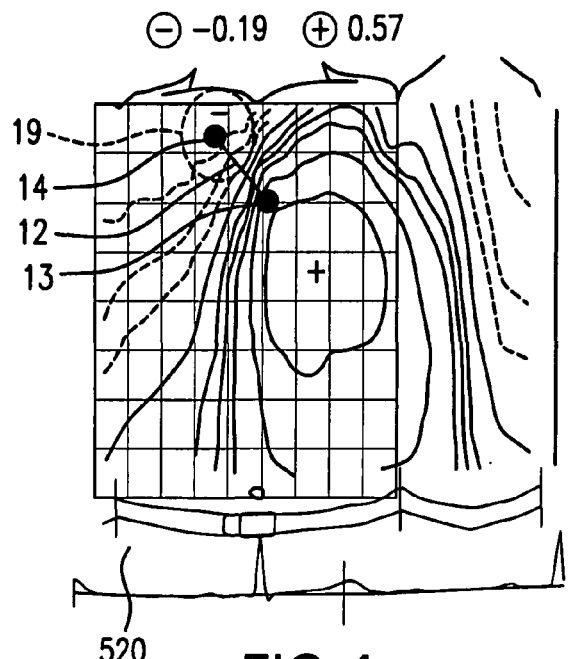
FIG. 4*c* shows body surface maps during the peak T wave in a healthy resting person. The same electrode positions shown in FIG. 3*a* are shown in FIGS. 4*a*, 4*b* and 4*c*.

FIG. 4c shows a body surface map of a healthy resting person at the peak of the T wave. Lead 12 would record a positive T-wave, which is consistent with the positive T-wave shown in waveform 700b in FIG. 3b. The timing of the peak of the lead 12 T-wave, as well as other aspects pertaining to the ST and U segments, may be used to diagnose ischemia, as will be further described below.

FIG. 4c also shows an alternative configuration of electrodes in the form of a ring 19 placed in the area of the upper right shoulder so that the area of the normal T-wave minimum is surrounded by the ring 19. The ring 19 may take the form of as little as 4 electrodes in a cross-bar configuration or many more electrodes. By surrounding the area of the normal minimum during both the T-wave and the early portion of the QRS, the ring 19 could be used to detect timing related aspects pertaining to the early QRS complex and T-wave. The time at which a minimum arrives within the ring 19, and the duration the minimum persists, may be assessed for both the early QRS complex and the T wave. This assessment provides information regarding the coverage of cardiac wavefronts over the ventricles.

For example, if a patient has posterior ischemia, the closure of the QRS wavefront around the ventricle will take longer than normal, and the potential minimum on the body will be on the back at a time when it should be (in healthy individuals) within the ring 19. Similarly, abnormally early repolarization of the endocardium (compared to epicardium) will cause a delay in the time the minimum shifts to within the ring. (Kubota et al., Detection of diseased coronary artery by exercise ST-T maps in patients with effort angina pectoris, single-vessel disease, and normal ST-T wave on electrocardiogram at rest, Circulation. 1989 July; 80(1): 120-7.)

The ring 19 may also be used to assess the strength of current flow into the minimum at selected times during the early QRS and T wave. A decrease in current flow towards the minimum, or a reversal of current whereby current flows from the center of the ring 19 to the perimeter, suggests a reduced amplitude of endocardial transmembrane potentials and/or early repolarization of the endocardium, both of which may be indicative of subendocardial ischemia. (Green et al., Detection and localization of coronary artery disease with body surface mapping in patients with normal electrocardiograms. Circulation. 1987 December; 76(6):1290-7.)

Flowcharts

FIGS. 5-8 are collectively a graphical representation of a functional flowchart for the preferred QRS onset and offset detection scheme which is accomplished according to the present invention. The flow chart is implemented by the architecture shown in FIGS. 1 and 2.

Figure 5:
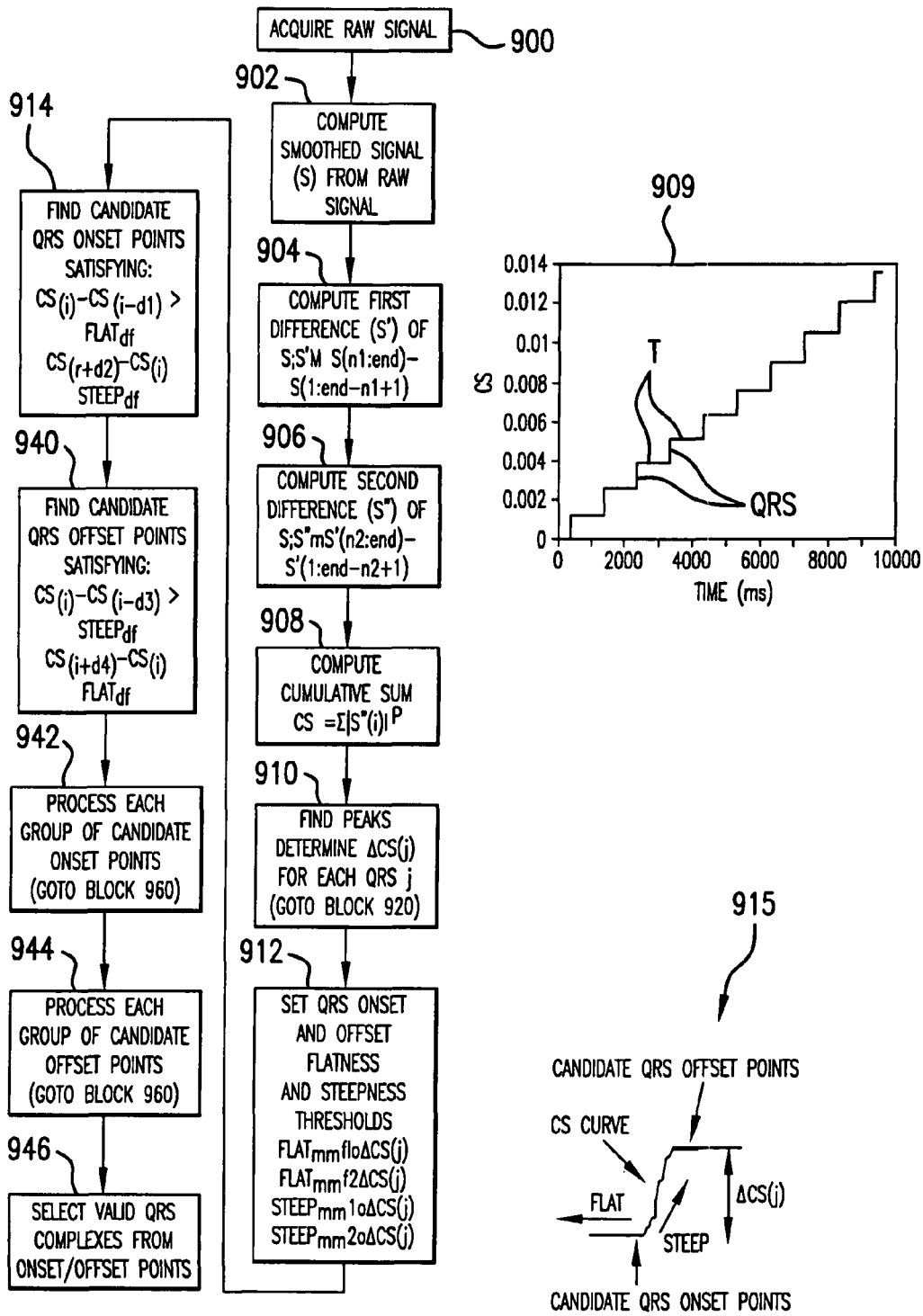
FIGS. 5-8 are collectively a flowchart of the preferred QRS onset and offset detection scheme according to the present invention.

In block 900 in FIG. 5, the system acquires waveforms corresponding to leads 15 and 12. A number of beats are acquired and processed as a group or 'segment', as described in U.S. patent application publication number 20070093720, which also discloses details regarding the acquisition of waveforms. Rather than a raw 'segment', an average segment may be used. The sampling rate is assumed to be 1kHz; the specific number of samples referred to with respect to various operations may be scaled to different sampling rates. In the flowchart, MATLAB notation is used to index vectors.

In block 902, the signal is smoothed by computing a 15 sample centered running average (i.e. 7 samples on either side of a middle sample), thereby generating a smoothed version of the signal which will be referred to as waveform S. In block 904, the first derivative of S is computed according to a centered difference scheme (i.e. n1 is equal to 3), thereby generating S'. Depending on the characteristics of the signal, it may be desirable to take a "longer distance" centered difference (i.e. n1>3). In block 906, the second derivative (S") of S is computed by calculating a centered difference of S'. Again, n2 is preferably set equal to 3 (standard centered differences) but may be adjusted. If the data is noisy, S' may also be smoothed with a running average filter.

In block 908, the cumulative sum (CS) of a function applied to each term S" (i) is computed. In the preferred embodiment, the function is $f((S"(i)))=(S"(i))^p$, where p is preferably 3. This function effects a high pass filtering of the second derivative S" (The compound function $g(i)=(S"(i))^p$ is a curvature function with a one-to-one time series correspondence with S that may be used to detect ischemia, as will be further described below). As such, a band-pass or high-pass filter may be substituted for the operation of taking the second derivative, although this is computationally more complex, requiring more energy from the implanted device. Further, multiple values of p, n1 and n2 may be assessed and subsequently selected by a physician. As applied to standard surface ECG leads, setting p=3 tends to filter out most or all of the P and T wave portions of ECG waveforms. The resulting cumulative sum CS has a staircase like form, as indicated in the drawing 909 to the right of box 908, in which the vertical jumps in the staircase correspond to the QRS complexes within the signal. Two QRS and T waves are indicated in the figure; the T waves leave very little imprint on the CS curve.

In block 910, a subroutine starting at block 920 (FIG. 6) is called that finds both a single peak for each QRS complex and the change in the value of CS, ΔCS(j), associated with each QRS complex j. An example of a ΔCS(j) is shown in the drawing 915 to the right of block 914. The ΔCS(j) for each QRS is used to identify candidate QRS onset and offset points by locating points that lie near the corners of the stairstep CS curve. The corners are characterized by a flat CS in one direction and a large jump in CS in the other direction; the large jump in CS should be a sizeable fraction of ΔCS(j). The flatness and steepness criteria are described more formally with respect to blocks 912, 914 and 916.

Block 912 sets steepness and flatness thresholds for both QRS onset and offset points that correspond to the steepness and flatness criteria mentioned above. For QRS onset points, the flatness criterion is that a first selected point should be located a particular distance to the left of a prospective QRS onset point (see drawing 915) should have a CS value that is close to the CS value (CS(i)) of the prospective QRS onset point. "Close to" is preferably defined with respect to the ΔCS(j) associated with the candidate QRS onset point; defining "close to" in this manner enables the system to adapt to CS curves with differing magnitudes. More particularly, "close to" for candidate QRS onset points is equal to f1*ΔCS(j), where f1 is preferably set to 0.02. A different threshold, f2, is applied to points to the right of candidate QRS offset points. A preferred value of f2 is 0.013. A more stringent flatness criterion for QRS offset points (i.e. f2<f1) helps to bias candidate QRS offset points away from the T wave.

The steepness thresholds are s1*ΔCS(j) and s2*ΔCS(j) for QRS onset and offset points, respectively, with s1 and s2 preferably set to 0.5.

In block 914, candidate QRS onset points are located by applying the f1 and s1 thresholds to the CS values at samples (points) to the left and right, respectively, of each prospective QRS onset point. To satisfy the flatness criteria, a sample that is a distance defined as 'd1' samples to the left of the prospective QRS onset point is chosen, and its CS value determined. The value of d1 in the preferred embodiment is 9. To satisfy the steepness criteria, a sample a sample that is a distance defined as 'd2' samples to the right of the prospective QRS onset point is chosen, and its CS value determined. The value of d2 in the preferred embodiment is 90, which is sufficiently long to enable detection of ectopic beats, which may have a somewhat less steep (but longer) CS jump than normal beats. It will be appreciated that more than one point to the left or right of a prospective QRS onset point may be selected, and different thresholds may be applied to each point. Further, instead of a simple thresholding function, a more complicated non-linear function of more than two neighboring points may be employed. It is well known that, multivariate measures, may be generated by combining the results of several of the described operations. Moreover, population and self-normative data may be used to adjust the values used for d1-3, n1-n3, a1-a4, p, and other values described herein and thereby increase sensitivity and specificity of the analysis.

In block 940, candidate QRS offset points are located in a manner analogous to the finding of QRS onset points described above. The parameter d3 is preferably equal to 105 and the parameter d3 is preferably equal to 9. In blocks 942 and 944, groups of QRS onset points and offset points are processed (in the routine starting at block 960), resulting in the choice of a single point within each group that will be the QRS onset or offset point for the corresponding QRS complex.

Figure 6:
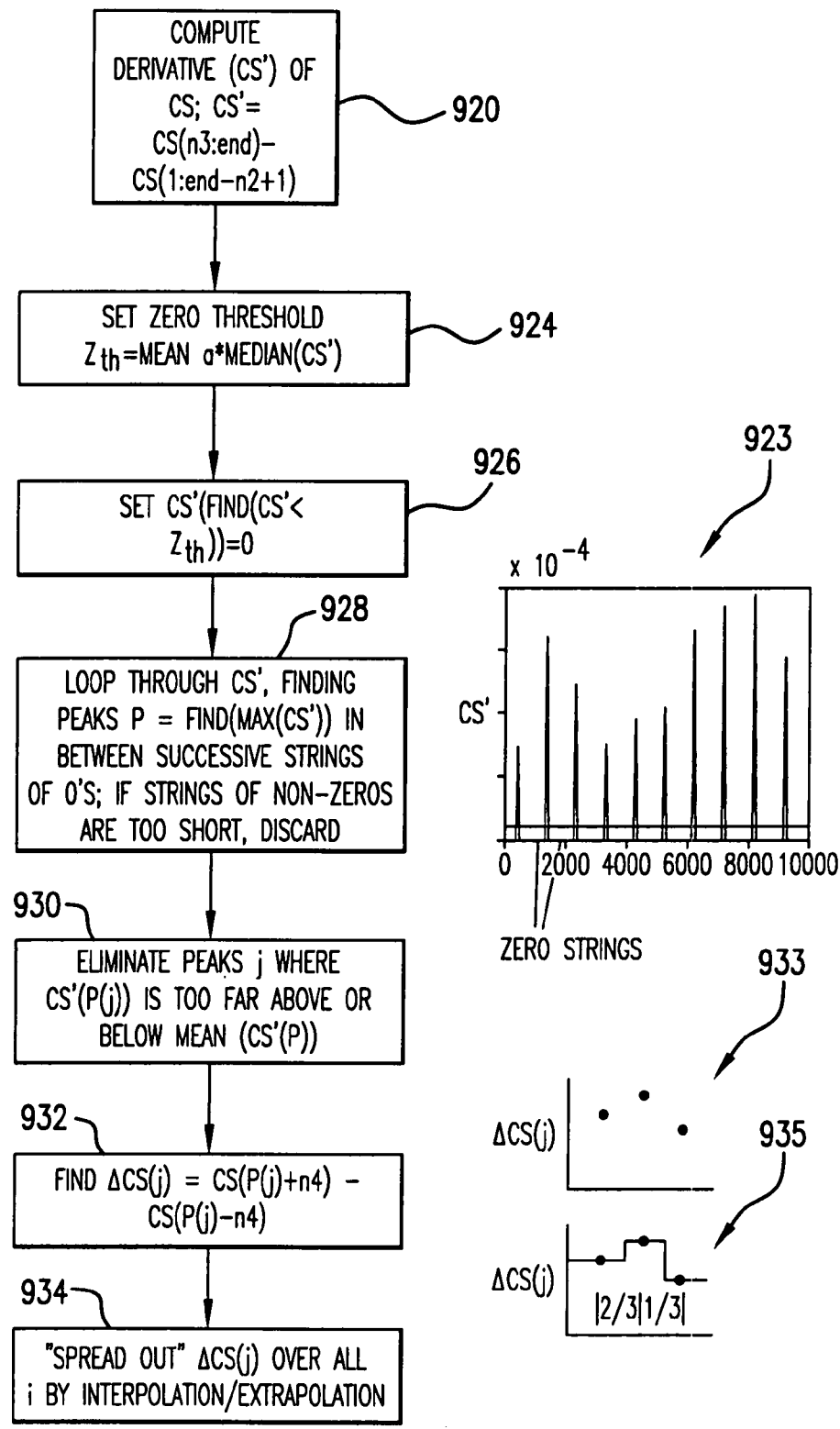

FIG. 6 is a flow chart of the peak detection and ΔCS(j) computation routine called by block 910 (FIG. 5a). In block 920, a centered difference (n3=3) of CS is computed, thereby generating waveform CS', which represents the change in the CS waveform, which has its largest value at the samples/points characterized by the sharpest QRS peak. Since CS' is the difference of a sum of terms $|S''(i)|^p$, it is closely related to the terms $|S''(i)|^p$. (Analogously, the derivative of an integral is equal to the integrand.) Indeed, instead of computing a centered difference of CS, the individual terms $|S''(i)|^p$ could be used to determine the sample i corresponding to the sharpest QRS peak. In the preferred embodiment, the centered difference formula is used because it tends to further enhance peaks compared to using just the individual terms $|S''(i)|^p$.

As will be further described below and referring to drawing 923, the peak detection routine defines peaks as those points that have the largest CS' value in between a number of points where CS' is defined as 0 ("zero strings"). The zero strings surrounding the second peak in CS' are indicated in drawing 923. CS' is defined as 0 for all points where CS' is less than a certain threshold, which is determined in block 924. The threshold is graphically depicted by a dashed horizontal line in drawing 923.

In block 924, the zero threshold is defined as 500 times the median value of CS' (i.e., with reference to block 924, a=500). In block 926, all values of CS' less than the zero threshold are set to 0. In block 928, CS' is searched to find the peaks by finding the maximum value of CS' in between strings of at least 40 consecutive zeros. However, if the consecutive string of non-zeros is too short, less than 30 samples, it may represent noise and is discarded. In this example, 30 samples is far less then the width of even a narrow QRS; however, some ischemic QRS's may have relatively low high frequency content, in which case their associated jumps in CS may occur over a relatively short time. As a further protection against noise, or a very sharp T-wave, characterized by a very small CS' value. To eliminate these outliers, block 930 computes the mean CS' at the peaks (e.g. 10 CS' values would be computed with respect to the data shown in drawing 923) and eliminates those peaks that: (i) are more or less than 3 standard deviations away from the mean value; or (ii) are less than $\frac{1}{50}^{th}$ of the "typical maximum value" of CS', which is defined as the mean value of CS' plus the standard deviation of CS'.

Having located valid peaks P, ΔCS(j) (see drawing 915 in FIG. 6) is derived by computing the size of the "jump" in CS around each peak P. More formally, for QRS j, ΔCS(j)=CS(P(j)+60)−CS(P(j)−60). In this case, n4=60, which means that ΔCS(j) is determined by the jump in CS between the 120 samples centered on the peak (P(j)). Since ΔCS(j) is defined only for the peaks j, as shown in drawing 933, and must be computed for each sample point, ΔCS(j) at the peaks must be interpolated/extrapolated. This is shown in drawing 935 and is also indicated in block 934. In the preferred embodiment, the value associated with a peak is extended $\frac{2}{3}$ of the distance after, and $\frac{1}{3}$ of the distance before, that peak, as indicated in drawing 935. This type of biasing further assists in the rejection/isolation/detection of T-wave data.

Figure 7:
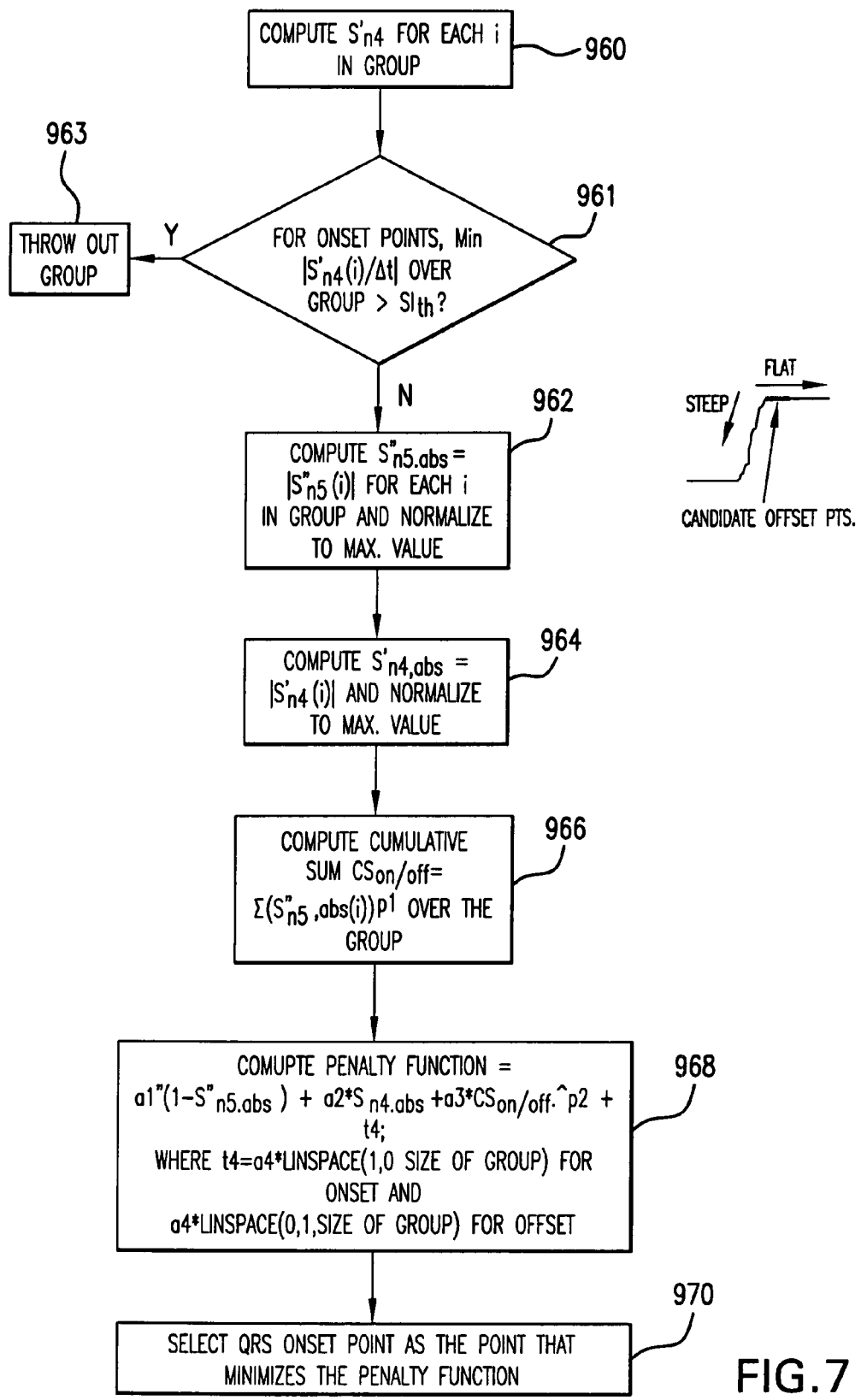

FIG. 7 is a flow chart of the QRS onset/offset selection routine called by block 942 (FIG. 5). In block 960, a centered difference is computed for each point in the group. In block 960, the subscript n4 indicates the distance, in number of samples, employed in the differencing. For example, in the preferred embodiment, block 960 involves a simple centered difference scheme, which entails computing terms like s(i+1)−s(i−1), where s is the signal being differenced. In this case, n4=1, which indicates that one sample to the right and one sample to the left are used in the computation of slope. Since a simple centered difference was computed in block 904, it need not be recomputed if the values of S' (see block 904) are stored and are thus available.

In block 961, for groups of onset points, the minimum slope $|S'(i)/\Delta t|$ over all the members in the group, where $\Delta t$ is the sampling period, is compared to a threshold. If this value is too great, then the group does not represent a true QRS onset (it may be the rise of a T wave or noise) and is thrown out in block 963.

Otherwise, processing continues in block 962, where a "long distance" difference of waveform $S'_{n4}$ is computed ($S'_{n4}(i+20)-S'_{n4}(i-20)$), thereby generating waveform $S''_{n5}$, with n5=20. (If there are less than 41 samples in the group, then n5=floor((n−1)/2), where n is the number of samples in the group.) The absolute value of $S''_{n5}$ is computed and the result is normalized to the largest value, so that $S''_{n5,abs}$ varies between 0 and 1. ($S''_{n5,abs}$ may be thought of as having been generated by a single global curvature function.) In block 964, the absolute value of $S'_{n4}$ is computed and the result normalized so that $S'_{n4,abs}$ varies between 0 and 1.

In block 966, the cumulative sum $CS_{on/off}$ of $S''_{n5,abs}$ is computed (i.e. p1=1; if p1 is even, the absolute value of $S''_{n5}$ need not be computed in block 962).

In block 968, a penalty function is computed such that the sample/point at which the penalty function is at a minimum is chosen as the QRS onset or offset point within the subsignal waveform defined by the group of candidate QRS onset/offset points. There are four terms in the penalty function, which bias the choice of the QRS onset/offset points toward that portion of the subsignal: (i) with a smaller first difference (i.e. flatter part of the subsignal); (ii) with a larger second "long distance" difference (which along with the flatness mentioned above, tends to correspond to an inflection point); (iii) not within the QRS complex, where points outside of the QRS complex are evidenced by a smaller value of $CS_{on/off}$; and (iv) that is relatively closer to the QRS complex as indicated simply by the relative order within the group of candidate points, which is reflected by the fourth term in the equation, which is labeled as 't4'.

With regard to item (iv), an example helps illustrate the implementation of the t4 term. If there are 40 candidate onset points, the furthest point to the left (i.e. the earliest point in time), is assigned a t4 value of 1 whereas the $40^{th}$ (last) point in the group is assigned a value of 0. The smaller value, 0, is more likely to be the QRS onset point because the QRS onset point is chosen at the minimum value of the penalty function. An analogous example shows how t4 is computed for QRS offset points. If there are 40 candidate offset points, the furthest point to the left/earliest point in time, is assigned a t4 value of 0 whereas the $40^{th}$ point in the group is assigned a value of 1.

The coefficients a1, a2, a3 and a4 are preferably equal to 1, 3, 10 and 5, respectively. Concerning the third term, each member of $CS_{on/off}$ is preferably squared (i.e. p2=2) to help sharpen the difference between points in and out of the QRS complex.

In block 970, as mentioned, the onset or offset point is selected as the point which the penalty function is at a minimum.

Figure 8:
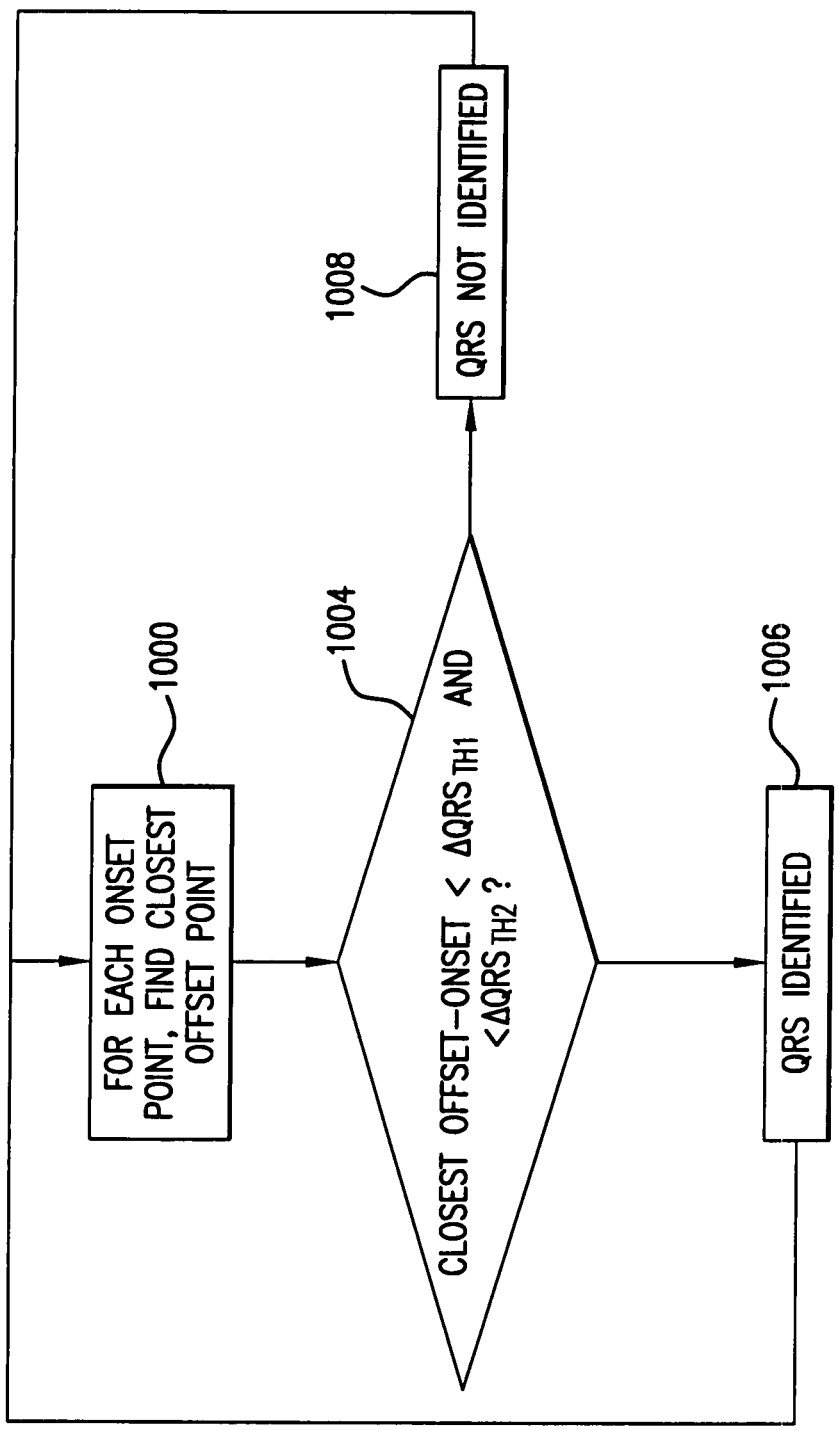

FIG. 8 is a flowchart of the routine, called by block 946 (FIG. 5), that selects valid QRS complexes given sets of QRS onset and offset points. In block 1000, for each QRS onset point, the closest QRS offset point after the QRS onset point is located. For example, if a particular QRS onset point is located at sample number 1022, and the set of QRS offset points is [21 1110 2130 3001], the sample 1110 is selected as the QRS offset point that pairs with onset point 1022. In block 1002, the routine determines whether the time interval between the onset and offset points (e.g. 1110 ms−1022 ms=88 ms in the above example) is less than a first specified threshold and less than a second specified threshold. If so, then the onset/offset pair defines a valid QRS, as shown in block 1006. Otherwise, the onset point does not define the start of a valid QRS (e.g it could potentially be the start of a T-wave).

The duration of a particular QRS complex, as well as the RR interval between it and the preceding QRS complex, may be examined to determine if the particular QRS complex is an ectopic beat. Ectopic beats may further be identified by their $\Delta CS(j)$ value, which tend to be larger than normal. A similar but better distinguishing metric for ectopic beats would be to compute the jump in the cumulative sum of S' (see block 904 in FIG. 5), which tends to be larger for ectopic beats. Self-normative thresholds for ectopic beat detection can be computed for S'.

Figure 9:
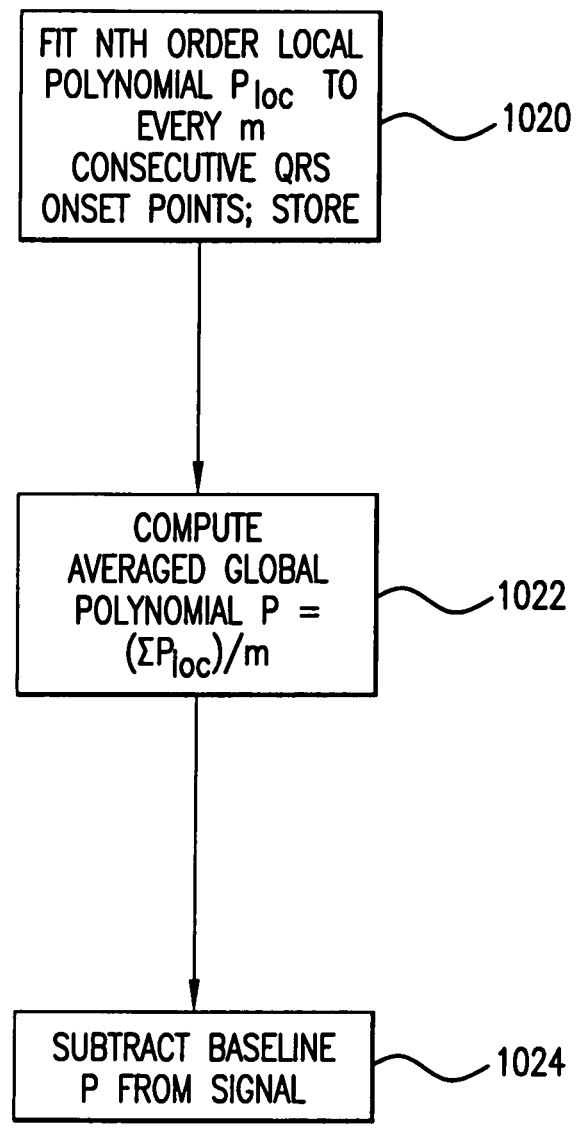
FIG. 9 is a block diagram of the preferred baseline correction routine.

FIG. 9 is a block diagram of the preferred baseline correction routine. In outline, the routine computes splines that connect the QRS onset points of every 3 consecutive QRS complexes. The splines are then averaged to create a single baseline correction waveform. In block 1020, an nth order local polynomial (spline) is fitted to every m consecutive QRS onset points. In the preferred embodiment, a quadratic polynomial (n=2) is fitted to every 3 consecutive onset points (m=3). In block 1022, all of the local polynomials are averaged together. Apart from the first and last two onset points, each onset point will have been fitted to three different local polynomials. The three overlapping polynomials at most points are added together and divided by three, resulting in a global baseline offset polynomial. (Some points towards the beginning and end of the data sequence are associated with one or two polynomials and are not averaged (if there is only 1 polynomial) or are averaged by dividing by two (in the case of two polynomials).) In block 1024, the global baseline polynomial P is then subtracted from the raw signal, resulting in a baseline-corrected signal.

Figure 10:
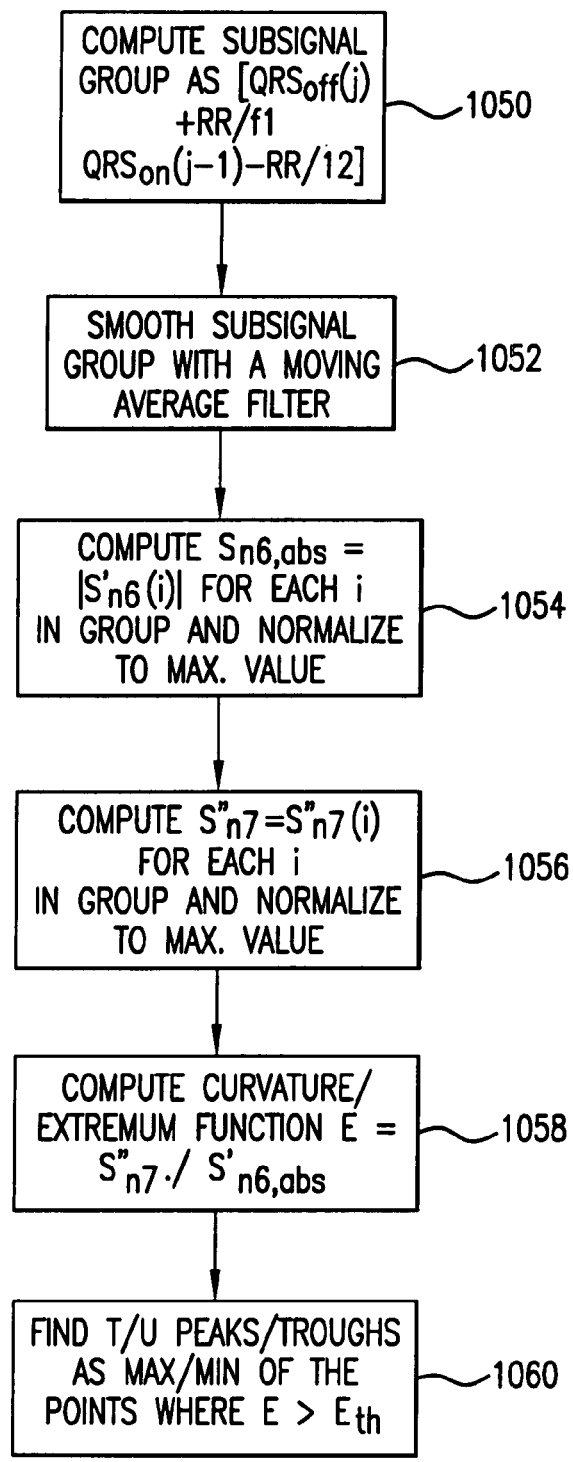
FIG. 10 is a flow chart of the routine that is used to find T/U wave peaks.

FIG. 10 is a flow chart of the routine that is used to find T/U wave peaks. First, in block 1050, for any particular QRS, the group of points/samples in which the T/U waves occur is selected. For a particular QRS, the first point in the group is equal to the QRS offset for that QRS plus a time lag within which the T wave can not occur. This time lag is equal to the RR interval between the QRS and the subsequent QRS divided by a factor f1, which is preferably equal to 10. The last point in the group is equal to the QRS onset for the following QRS less a time lag within which the T/U waves should not occur. This time lag is equal to the RR interval between the QRS and the subsequent QRS divided by a factor f2, which is preferably equal to 2. The above time lags are valid for non-ectopic beats.

In block 1052, the subsignal represented by the group computed in block 1050 is smoothed with a simple moving average filter that computes the smoothed subsignal at any sample/point as equal to the average of that sample along with the 45 samples to the left and right of that sample. (Compared to the QRS portion of the waveform, the T and U wave portions have lower frequency components, which means that relatively greater smoothing can be employed for the T/U wave portion of the waveform without loss of desirable information.)

In block 1054, the derivative S'n6 is computed from the smoothed subsignal waveform, where again the subscript n6, preferably equal to 1, indicates the number of samples involved in the differencing (s(i+1)−s(i−1)). The absolute value of S'$_{n6}$ is computed and the resulting signal is normalized to a maximum value of 1.

In block 1056, the derivative S"$_{n7}$ is computed from S'$_{n6}$, with n7 preferably equal to 10. Since the peaks of the T/U waves can be somewhat flat, the relatively large value of the differencing (10), allows waveform curvature (second derivative) to be computed over a longer "distance." S"$_{n7}$ is normalized to a maximum value of 1.

In block 1058, the curvature extremum function E=S"$_{n7}$/S'$_{n6}$ is computed. This function tends to have spikes when the smoothed subsignal is flat (i.e. S'$_{n6}$ is small.) In block 1060, the T/U extrema are selected as those points where the smoothed subsignal is at a maximum/minimum and the extremum function E is above a threshold. The threshold is preferably equal to 0.5*mean(E). By requiring E to be above this threshold, only those maximum and minimum points corresponding to a peak/trough are selected. (The largest minimum point need not occur at the minimum of the trough; for example, if there is a negative T wave, the maximum value of the subsignal may be at the start of the ST segment.)

Figures 11, 12:
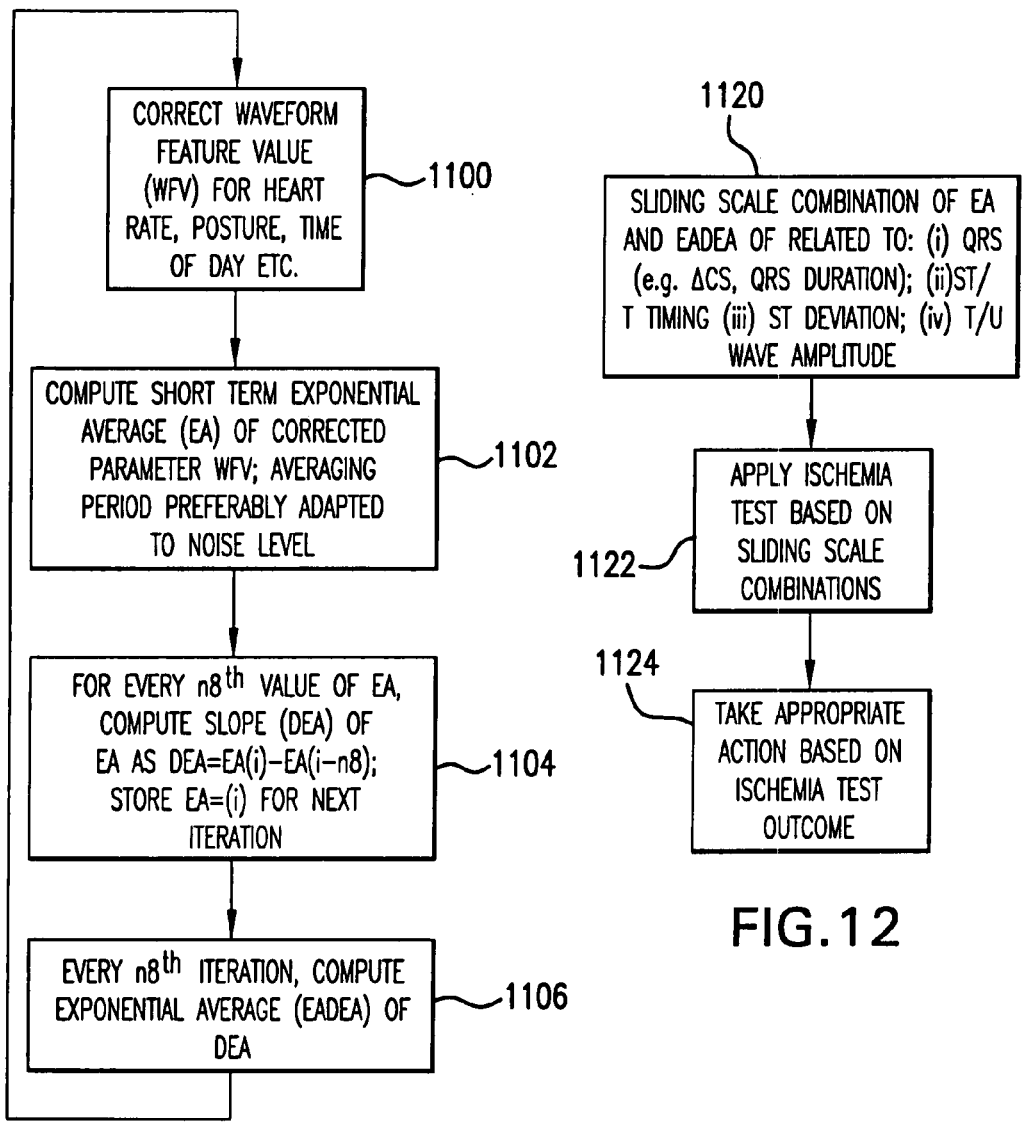
FIG. 11 is a flow chart of a routine for extracting waveform feature values that in turn are used to compute a likelihood of ischemia.
FIG. 12 is a flow chart of a routine for computing a measure of the likelihood of ischemia based on waveform feature values.

FIG. 11 is a flow chart of a routine for extracting waveform feature values that in turn are used to compute a likelihood of ischemia (i.e. apply an ischemia test), as will be further described with reference to FIG. 12. In block 1100, a waveform feature value (e.g. ACS, duration of period between QRS offset and peak T wave) is corrected for heart rate and posture. Additionally, some waveform feature values may be corrected for time of day. For example, it is known that the QT interval has circadian variations. As mentioned in the Limited Lead Set Application, posture information may be extracted from an analysis of the cardiac waveform and/or obtained through the use of sensors such as accelerometers. Regarding heart rate, corrections are preferably patient specific (i.e. for a particular patient, waveform feature values are recorded at different heart rates in a variety of postures and other patient states). For example, in normal circumstances, the duration of the period between QRS offset and peak T wave decreases with increases in heart rate. (There are many known general formulae for correcting a related duration, the QT interval; Bazett's formula is the most commonly used in clinical settings.) The $i^{th}$ corrected waveform feature value will be referred to as WVF(i).

In block 1102, the exponential average is defined as EA(i)=α*(WVF(i))+(1−α)*EA(i−1). The value of α is preferably noise dependent, such that noisier data is processed with a smaller value of α. The noise level of the data may be estimated in a number of ways, e.g. by computing the standard deviation of every 10 consecutive WVF's. The value of α is preferably small enough to properly smooth the data but large enough to capture real short term trends in the data. An α value of 1/10 was used to generate the graph shown in FIG. 15a and FIG. 16c. This value of α (1/10) is an estimate of the moving average of the WVF over 10 beats. (How closely EA matches the true average of the past 10 WVF's depends on the characteristics of the data.) A 10 beat average generally is long enough to smooth out the effects of breathing, which (at resting heart rates) results in noise generally in the frequency range of 0.2 Hz-0.5 Hz but α may need to be adjusted depending on a person's ratio of heart rate to breathing frequency.

In block 1104, for every $n8^{th}$ iteration, the slope of the EA curve (across n8 values) (hereafter termed DEA) is computed as DEA(j)=EA(i)−EA(i−n8), where the index j=floor (i/n8) The value of n8 should be large enough to avoid reflecting short term fluctuations (e.g. over a few beats) but small enough to provide information regarding the long term trend of EA. In the graph shown in FIG. 15b, n8 was set to 20. In block 1106, if there is a new value of DEA (i.e. if the current iteration is an $n8^{th}$ iteration such that j has been incremented), the exponential average of DEA is computed as EADEA(j)=a*(DEA(j))+(1−a)*DEA(j−1). A value of a=1/10 was used to produce the graphs shown in FIGS. 15b and 17b. With n8=20 and a=1/10, DEA(j) is an approximation of the average slope of EA over 200 beats (20*1/(1/10)).

FIG. 12 is a flow chart for applying an ischemia test based on the EA and DEA of various waveform feature values. In block 1120, the EA and EADEA values for a variety of waveform feature values are combined in a sliding scale manner to derive a likelihood of ischemia factor for that waveform feature. The more that the EA of a WFV varies from its normal value, the greater the likelihood of ischemia according to the outcome of the test. Preferred WFV's to utilize include QRS related measures, an example of which will be discussed below and other examples of which were discussed with reference to FIGS. 3 and 4, T wave timing measures, ST segment deviation (difference between signal amplitudes at QRS offset and onset and/or minimum amplitude between QRS offset and peak T wave); and T/U wave amplitude.

The rate of change of the EA conveys independent information regarding the likelihood of ischemia. In particular, if an EA has a large average slope over a number of minutes, a pathophysiological cause is suggested since other causes that operate over smaller and larger time frames, such as axis shifts and physiological adaptations respectively, would not result in a large EADEA. The EADEA serves as a rate of change metric for its associated WFV.

The sliding scale factors are preferably based on patient specific data. For example, if a patient's standard deviation of an EA for a waveform factor is SD$_{wvf}$ and the patient's standard deviation of the EADEA for waveform factor is SD$_{slope}$, then a table such as the following may be constructed (based on the simplifying assumption of a 0 mean):

| Value of EA | Value of EADEA | Likelihood of ischemia |
|---|---|---|
| 1.5 * SD$_{wvf}$ | 3 * SD$_{slope}$ | 0.8 |
| 2 * SD$_{wvf}$ | SD$_{slope}$ | 0.8 |
| 3 * SD$_{wvf}$ | | 0.9 |

Figure 15B:
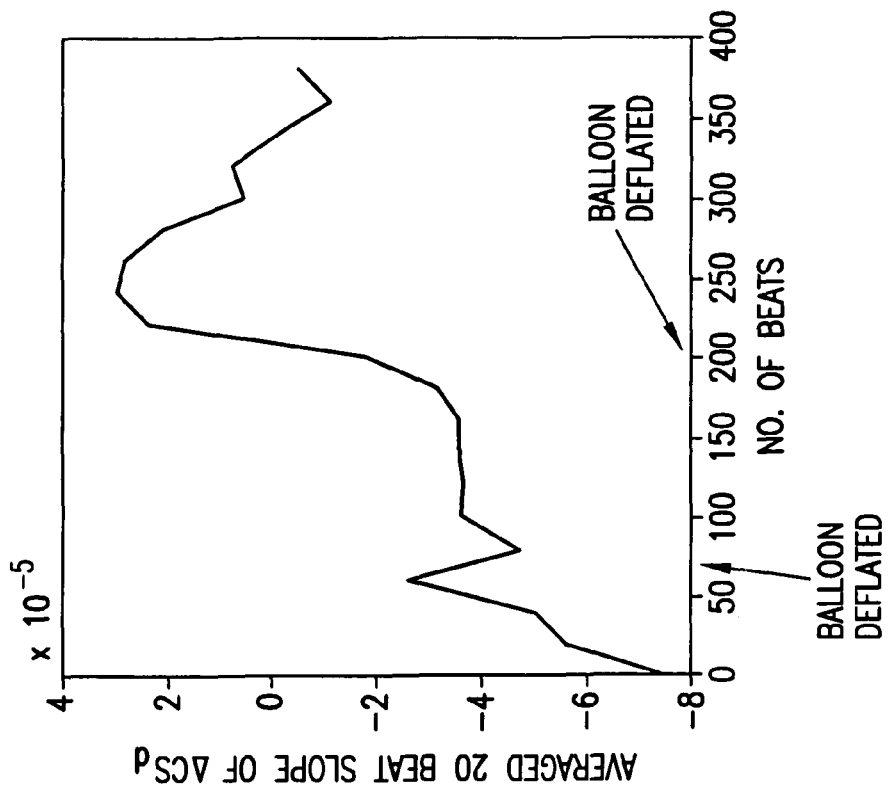
FIG. 15*b* shows a measure of the long term slope of the waveform shown in FIG. 15*a*.

A specific example of the use of both the EA and EADEA will be described with reference to FIGS. 15a and 15b, which show the EA and EADEA of a QRS related waveform feature value (described more fully below) during balloon angioplasty. (This data is not publicly available.) The balloon was inflated at approximately 50-60 beats. The QRS related waveform feature value represented by the dashed line decreases by 50% after approximately 200 beats, after which the balloon was deflated. FIG. 15b shows that this WFV was steadily decreasing over a relatively large number of beats (i.e. 200 beats, as described with respect to block 1106 in FIG. 11). For this parameter, an EA of <0.0002 with an associated EADEA of <−0.00003 units/20 beats may indicate a high likelihood of ischemia.

Figure 17B:
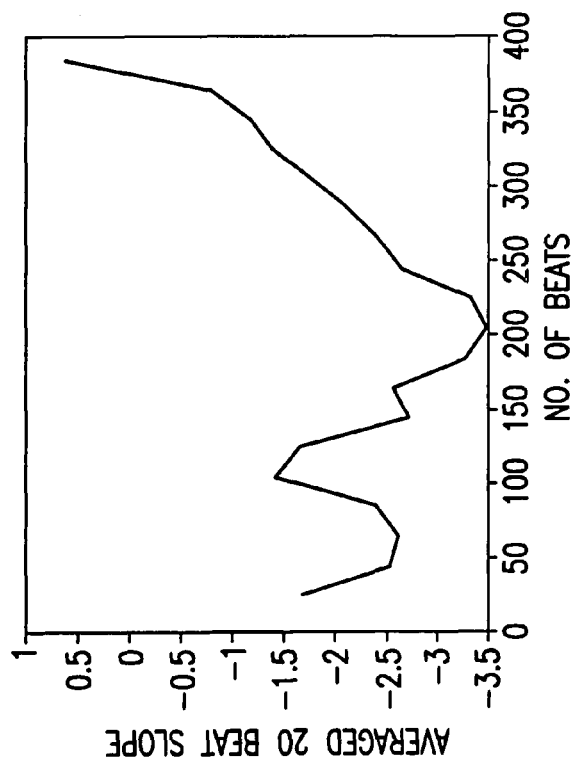
FIG. 17*b* shows the long term slope of the waveform shown in FIG. 17*a*.
Figure 17A:
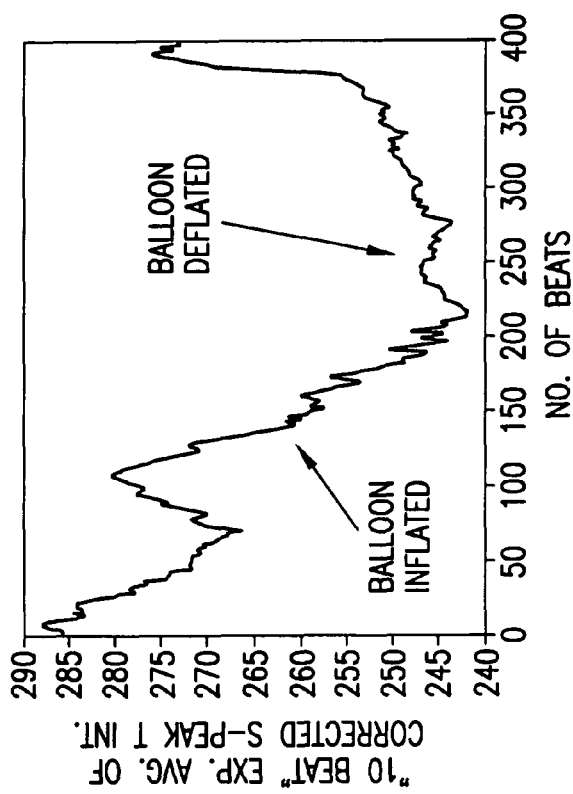
FIG. 17*a* shows an exponential average of the QRS offset to peak T wave interval in a patient undergoing balloon angioplasty.

FIGS. 17a and 17b show more specific examples of both the EA and EADEA of a T wave timing related waveform feature value, the duration of the S to peak T segment divided by the square root of the RR interval, of a patient undergoing balloon angioplasty. (This data is not publicly available.) Although the exact balloon inflation time is not know, it is likely that it occurs just before the initial rise (around beat 60) of the corrected S to peak T duration. (Some data indicates that the first 20-40 ms of balloon inflation are associated with a lengthening of the corrected QT interval. Kenigsberg et al., J Am Coll Cardiol. 2007 Mar. 27; 49(12):1299-305.) For this patient, a corrected S to Peak T interval of 250 ms, with an associated long term decrease in this parameter of more than 2 ms/20 beats as shown in FIG. 17b, may correspond to a high likelihood of ischemia. (FIG. 17b was generated with an n8 value of 20; see block 1104 in FIG. 11.)

The measurement of another T wave timing factor, the interval between QRS offset and T wave onset, as defined according to a curvature metric, may help to assess whether ischemia has become transmural. The "knee" of the epicardial action potential may correspond to T wave onset. Transmural ischemia may tend to cause the entire epicardium to repolarize earlier than normal, so that the "knee" of the epicardial action potential is reached relatively sooner. Consequently, the interval between QRS offset and T wave onset would tend to decrease. The peak of the T wave may correspond to the endocardial action potentials reaching their knees, in which case QRS offset to peak T duration may be a more general indicator of ischemia (both subendocardial and transmural.)

In block 1122, likelihood of ischemia associated with individual WVF's may be combined, for example by the methods disclosed in the Limited Lead Set Application, to derive an overall likelihood of ischemia.

Figure 14B:
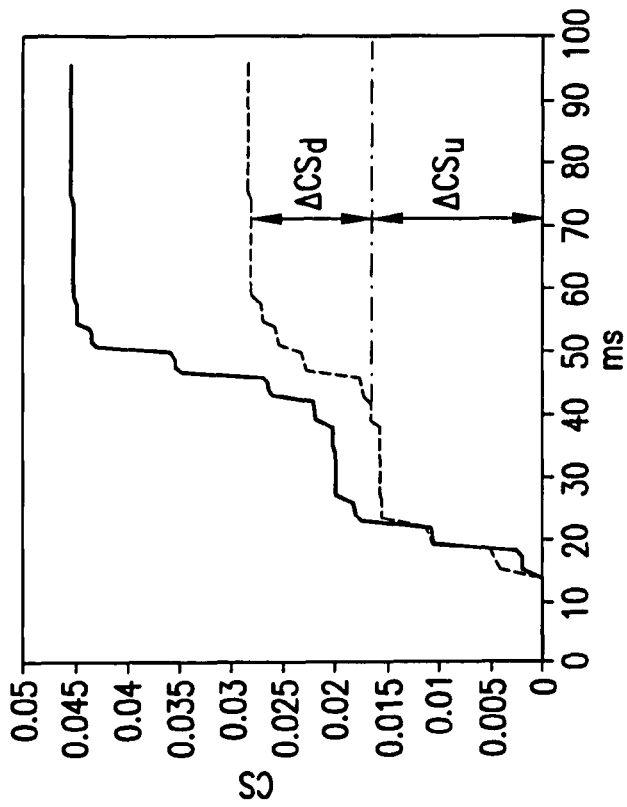
FIG. 14*b* shows the associated CS profiles of these waveforms.

The CS and T-wave components of FIG. 5 can be incorporated into a number of measures for which thresholds, confidence intervals, guard-bands, and self-norms may be computed. Additionally, similar to heart-rate, these measures may be used to classify cardiac activity into different classes (a 'steep-CS' class). For example, ratios can be computed between the CS duration (defined as the beginning to end of the CS segment, and which is also the slope measure without the y-axis information) and T-wave duration. Measures of the CS, such as slope may be computed upon the entire CS, or slope can be computed for bottom half of the CS, for the upper half of the CS, and measures can include ratios of between these two slopes. Additionally, measures such as amplitude or duration may be computed for different portions of the staircase, as is shown in FIG. 14b (which will be further described below).

When guard-bands applied to a data which are used to create the staircase of the type shown in FIG. 5, then each step of the staircase can be evaluated (e.g. right side of FIG. 7) or average steps can be computed and can be evaluated by the criteria. Similar to analysis of cardiac segments, when sequential steps are evaluated, the detection criteria can be applied across the segment, and further sliding scale criteria can be used.

Based on the likelihood of ischemia as computed above, an appropriate responsive action is taken, as suggested by block 1124. For example, if ischemia appears likely, the system may send an appropriate warning to the patient.

ORS Curvature Analysis

The background section described a method for analyzing the high frequency content of the QRS, which has been shown to be a possible ischemia marker. The inventor believes that the curvature of the QRS waveform, which will affect the high frequency content of that QRS, may be another ischemia marker. The following describes methods for generating a waveform feature value that is based on QRS curvature without the need for employing a recursive digital passband filter. (Preferably, as will be described below, exponential averaging, which is a recursive digital filter, is employed after these curvature dependent waveform feature values are generated to derive an average of these waveform feature values.) The following, in conjunction with the flowchart described with reference to FIG. 12, also describes methods for detecting ischemia based upon QRS curvature, however measured.

One measure of the curvature, $\Delta CS$, with is the cumulative sum of a curvature function $S''(i)^p$ and is therefore a type of global curvature function, was described in connection with FIGS. 5 and 6 (see drawing 915 in FIG. 5) in the context of locating QRS onset and offset points. FIGS. 13a and 13b illustrate how $\Delta CS$ (and CS) reflects waveform curvature. The solid and dashed lines in FIG. 13a show ½ cycle cosine waveforms at a baseline frequency and twice that frequency respectively. The high frequency waveform (dashed line) has reduced amplitude. Despite the reduced amplitude, the high frequency waveform has a much larger $\Delta CS$ than the lower frequency waveform, as indicated in FIG. 13b. If the higher and lower frequency waveforms are analogized to a healthy person's QRS at high and normal heart rates, respectively, FIGS. 13a and 13b suggest that $\Delta CS$ may track the changes in QRS with heart rate. Similarly, at a given heart rate, reductions in CS may suggest the presence of ischemia (or other pathologies.)

Figure 14A:
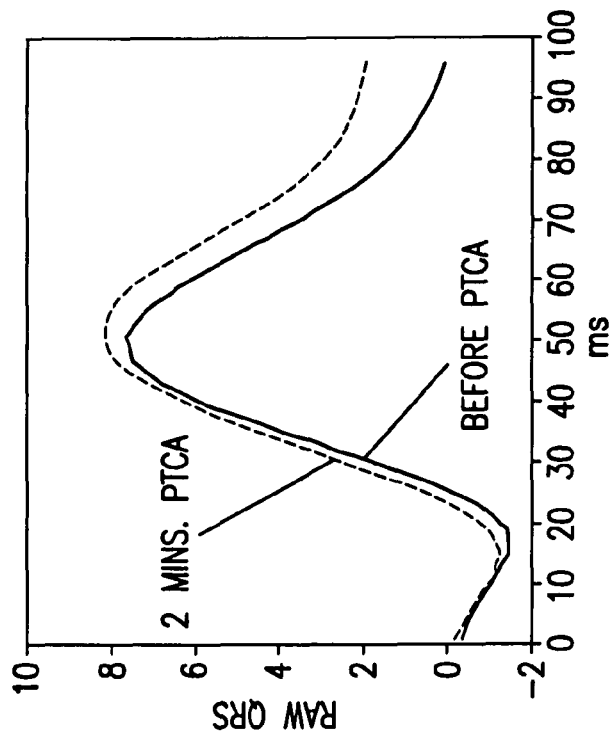
FIG. 14*a* shows QRS waveforms before and 2 minutes into a balloon inflation.

FIG. 14a shows QRS waveforms before (solid line) and 2 minutes into a balloon inflation. (This data is not publicly available.) FIG. 14b shows the associated CS profiles. The inflation CS is generally smaller. FIG. 14b also divides the change in CS between before (upstroke) and after (downstroke) the QRS peak, which occurs at approximately 50 ms. FIGS. 15a and 15b show changes in CS over time for the same patient/lead associated with the data in FIG. 14. FIG. 15a shows the EA of both the ACS upstroke ($\Delta CS_u$) and ACS downstroke ($\Delta CS_d$), associated with QRS upstroke and downstroke portions respectively, during the balloon inflation and deflation periods. $\Delta CS_d$ changes more, in percentage terms, than $\Delta CS_u$. FIG. 15b shows the EADEA of $\Delta CS_d$.

The rise in the $\Delta CS$, possibly just after balloon inflation, is consistent with the well known phenomenon of increase in propagation speed just after induction of ischemia. (This may occur for the same reason that propagation speed increases with heart rate in healthy persons; the ischemic cells simply "think" the heart rate is higher than it is. After some time, however, buildup of calcium in ischemic cells likely causes significant propagation slowing due to gap junction closure.) Furthermore, the existence of ischemia in one area of the heart could actually speed propagation in the healthy areas by decreasing electrical loading of those areas. In any event, some data both non-publicly available and publicly available (Pettersson et al., J Am Coll Cardiol. 2000 Nov. 15; 36(6): 1827-34) suggest that an increase in the high frequency content of the QRS, as measured by particular leads, after induction of ischemia may increase for a number of minutes. Thus, increases as well as decreases in CS/CS' are ischemia markers.

FIGS. 16a, 16b, and 16c show CS and CS' data from a lead II like lead placed on a healthy person both lying down and sitting up. (As mentioned in connection with block 920 of FIG. 6, since CS' is the difference of a sum of terms $|S''(i)|^p$, it is closely related to the terms $|S''(i)|^p$.) CS' is a curvature function with one to one time series correspondence with the QRS waveform from which CS' is computed. The CS and CS' profiles are different in the different postures, but these profiles do not vary as much as the changes in CS and CS' shown in FIG. 15.

Furthermore, a change in posture between lying down and sitting up would tend to cause a sharp change in CS, so that the longer term slope of CS (EADAD) would be relatively smaller than the slopes shown in FIG. 15b. Thus, as mentioned with respect to block 1120 (FIG. 12), EADAD can be used to distinguish shifts in EA's caused by ischemia and shifts caused by other factors. The data in FIGS. 16a, 16b, and 16c was generated by calculating CS without smoothing the raw signal S or its first difference S' (see blocks 902 and 904 of FIG. 5).

Figure 15A:
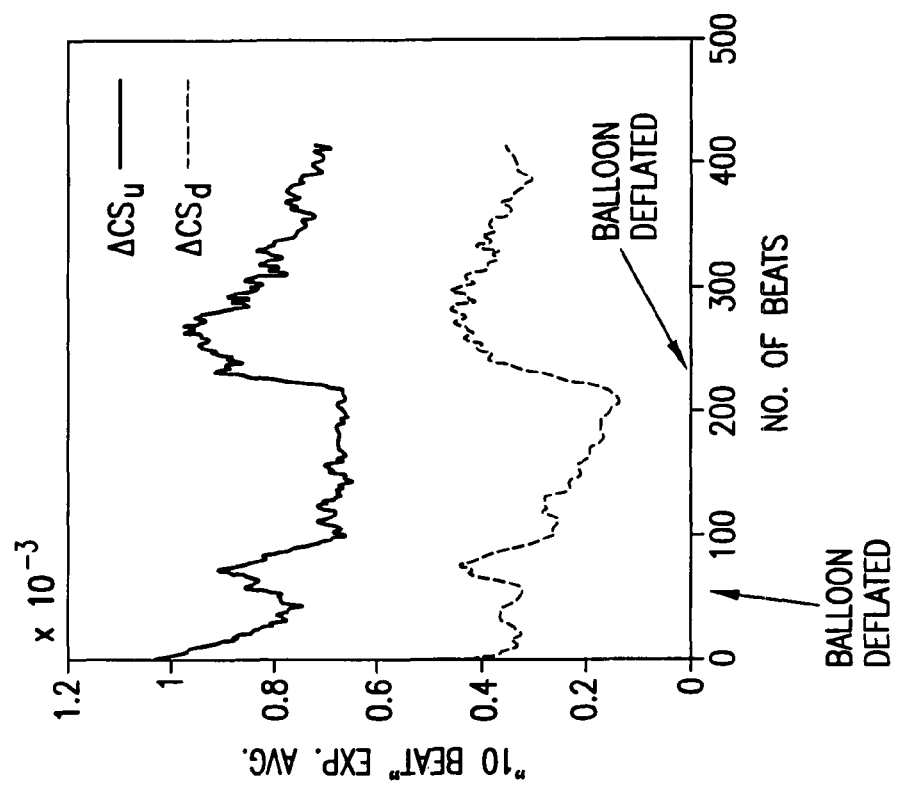
FIG. 15*a* shows an exponential average over hundreds of beats of a parameter related to CS during the same balloon occlusion referenced in FIG. 14*a*. Specifically, this parameter is the jump in CS associated with each QRS.

FIG. 16c also shows that the standard deviation of the data (STD) for both sitting up and lying down is smaller as a percentage of the mean (approximately 0.007/0.034 and 0.004/0.022 in the case of sitting up and lying down, respectively) than the change in CS associated with ischemia shown in FIG. 15a.

Similar to FIG. 14a, FIG. 18a shows QRS waveforms before (solid line) and 2 minutes into a balloon inflation of a different patient than the patent associated with the FIG. 13 data. (This data is not publicly available.) FIG. 18b shows the associated centered difference of CS (CS') before (solid line) and after (dashed line) balloon inflation. By comparing the amplitudes and timing of the three different peaks in the CS' waveform, labeled as Pk1, Pk2 and Pk3, the CS' profile may be used both to detect axis shifts and ischemia.

FIG. 18c shows how the amplitude of the largest peak, Pk2, changes over the course of a balloon inflation. (The plot is a "30 beat" exponential average of Pk2 amplitude.) In this case, the amplitude of Pk2 steadily decreases during the inflation and steadily but sharply increases thereafter. FIG. 18d shows how the timing of Pk3 changes over the course of a balloon inflation. (The plot is also a "30 beat" exponential average.) The time (relative to QRS onset) that this peak occurs generally increases over the course of the inflation and decreases thereafter. The average slope of the waveforms shown in FIGS. 18c and 18d, i.e. the EADEA's of these waveforms, may be computed in the manner previously described and used as part of an ischemia test in the manner described with respect to the flow chart of FIG. 12. Because these waveform feature values are likely to fluctuate with axis shifts even in the absence of ischemia, the EADEA analysis can help to prevent false positive ischemia test results because an axis shift is unlikely to result in a steady change in these waveform feature values over a large number (e.g. 30 or more) beats.

The function ACS is related to the total energy in the second derivative waveform S". If the second derivative S" is squared and summed (i.e. p=2 in block 908 of FIG. 5), the result is the total energy in S", which by Parseval's theorem is equal to the total energy of the Fourier transform of S" (F(S")), where F(X) represents the Fourier transform of function X. In turn, $F(S'')=f^2*F(S)$, where f is the frequency. Thus, CS (with p=2) is equal to the sum (across frequencies) of $f^2*F(S)$. It follows that CS (with p=2) is strongly correlated with the high frequencies in F(S); higher values of p would further emphasize higher frequencies. On the other hand, high frequency noise can be removed/controlled by smoothing the raw signal or its derivatives and/or by computing first and second derivatives/differences over a greater number of samples (e.g. setting n2 in block 906 of FIG. 5 to greater than 3).

There are other non-recursive methods for assessing waveform curvature. For example, a cubic spline could be fitted to the peak of a QRS complex and to points a fixed number of samples before and after the peak. The coefficients of the spline would contain information regarding the curvature at the peak. There are also recursive methods for assessing waveform curvature, such as bandpass filtering with a recursive digital filter. Analysis of a QRS'FFT can also yield information regarding waveform curvature.

ADDITIONAL EMBODIMENTS

Rather than leads, self powered sensors can be used to record activity, and can relay sensed data using wireless means such as RF, sound, or other method Signal averaging could be used to generate representative beats and the methods described herein could be applied to those representative beats. Sensors can be located in the heart, subcutaneously, on the skin or off the surface of the body (e.g. as in some magnetocardiography applications). Sensors can be of any type, including electrical, magnetic and optical.

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A device for assessing the condition of a mammalian heart, comprising:
   a lead comprising two sensors, a processor coupled to the lead, the processor configured to:
   (i) obtain a signal from the lead, and compute a waveform corresponding to the signal, the waveform being characterized by a plurality of QRS complexes;
   (ii) compute a plurality of values of a waveform feature from the waveform representing the values of the waveform feature over time;
   (iii) apply a first filter to the plurality of values of the waveform feature, thereby deriving a first time series filtered waveform;
   (iv) derive a differenced waveform from the filtered waveform defining a second time series waveform where the differenced waveform is an absolute difference of at least one waveform feature taken in consecutive time intervals within a time segment;
   (v) compute from the second time series differenced waveform, a measure of the rate of change in the waveform feature over said time segment where the measure of the rate of change of said waveform feature is calculated as a function of the summation of the absolute difference of said second time series waveform feature taken in consecutive time intervals over said time segment, thereby deriving a change metric; and
   (vi) apply a test to detect a pathological heart condition, wherein the test is based on the change metric.

2. The device of claim 1 wherein the measure of change in the waveform feature value over time is computed by further applying a second filter to the differenced waveform.

3. The device of claim 2 wherein both the first and second filters comprise an exponential average filter.

4. The device of claim 1 wherein the first filter is an exponential average filter.

5. The device of claim 1 wherein the differenced waveform is a first finite difference of the filtered waveform.

6. The device of claim 1 wherein the measure of change in the waveform feature value over time is an average over a plurality of values of the differenced waveform.

7. The device of claim 1 wherein the waveform feature is ST segment deviation.

* * * * *